United States Patent
Kitahashi et al.

(10) Patent No.: US 11,837,331 B2
(45) Date of Patent: Dec. 5, 2023

(54) INTEGRATION SYSTEM AND INTEGRATION METHOD

(71) Applicants: Japan Agency for Marine-Earth Science and Technology, Yokosuka (JP); TechnoSuruga Laboratory Co., Ltd., Shizuoka (JP)

(72) Inventors: Tomo Kitahashi, Yokosuka (JP); Miyuki Nishijima, Shizuoka (JP); Masafumi Shimotashiro, Yokosuka (JP)

(73) Assignees: Japan Agency for Marine-Earth Science and Technology, Yokosuka (JP); TechnoSuruga Laboratory Co., Ltd., Shizuoka (JP)

(*) Notice: Subject to any disclaimer, the term of this patent is extended or adjusted under 35 U.S.C. 154(b) by 903 days.

(21) Appl. No.: 16/321,436

(22) PCT Filed: Apr. 27, 2018

(86) PCT No.: PCT/JP2018/017300
§ 371 (c)(1),
(2) Date: Jan. 28, 2019

(87) PCT Pub. No.: WO2018/199326
PCT Pub. Date: Nov. 1, 2018

(65) Prior Publication Data
US 2021/0295953 A1    Sep. 23, 2021

(30) Foreign Application Priority Data

Apr. 28, 2017 (JP) .................... 2017-090809

(51) Int. Cl.
*G06F 16/00* (2019.01)
*G16B 50/30* (2019.01)
(Continued)

(52) U.S. Cl.
CPC ........... *G16B 50/30* (2019.02); *G06F 16/254* (2019.01); *G06F 16/51* (2019.01); *G16B 30/00* (2019.02); *G16B 50/20* (2019.02)

(58) Field of Classification Search
CPC ........ G16B 50/30; G16B 30/00; G16B 50/20; G06F 16/254; G06F 16/51; G06F 16/00; C12Q 1/6869; G06Q 50/10
(Continued)

(56) References Cited

U.S. PATENT DOCUMENTS 6,303,297 B1   10/2001  Lincoln et al.
2002/0064792 A1  5/2002  Lincoln et al.
(Continued)

FOREIGN PATENT DOCUMENTS

CN    001813063 A    8/2006
CN    103339632 A    10/2013
(Continued)

OTHER PUBLICATIONS

Notice for Reasons for Rejection, App. No. JP2019-514684, dated Jun. 9, 2020, 8 Pages.
(Continued)

*Primary Examiner* — Irete F Ehichioya
*Assistant Examiner* — Shirley D Hicks
(74) *Attorney, Agent, or Firm* — Berkeley Law & Technology Group, LLP

(57) ABSTRACT

An integration system comprising a biological image acquiring device which acquires, from a sample including biological particles which are a detection target, a biological image which is an image of the biological particles; a nucleotide sequence information acquiring device which acquires nucleotide sequence information of the biological particles; and an integration device which associates and registers the biological image and the nucleotide sequence information
(Continued)

acquired from the same type of biological particles in an integrated database.

12 Claims, 9 Drawing Sheets

(51) Int. Cl.
  *G16B 50/20* (2019.01)
  *G06F 16/51* (2019.01)
  *G06F 16/25* (2019.01)
  *G16B 30/00* (2019.01)
(58) Field of Classification Search
  USPC .................................................. 707/600–899
  See application file for complete search history.

(56) References Cited

U.S. PATENT DOCUMENTS

| 2007/0064990 | A1* | 3/2007 | Roth | .................... | G06V 20/695 |
| | | | | | 382/128 |
| 2015/0298091 | A1* | 10/2015 | Weitz | .................. | B01F 33/3011 |
| | | | | | 506/28 |
| 2015/0324969 | A1 | 11/2015 | Denbrok et al. | | |

FOREIGN PATENT DOCUMENTS

| JP | 06117886 | A | | 4/1994 | | |
| JP | 2003242154 | A | * | 8/2003 | ............. | G06F 19/20 |
| JP | 2008175769 | A | | 7/2008 | | |
| JP | 2010088335 | A | | 4/2010 | | |
| JP | 2014203322 | A1 | | 12/2014 | | |
| WO | 2014175427 | A1 | | 10/2014 | | |
| WO | 2014203322 | A1 | | 12/2014 | | |

OTHER PUBLICATIONS

Thomsen, et al., "Detection of a Diverse Marine Fish Fauna Using Environmental DNA from Seawater Samples," PLOS One, vol. 7, No. 8, 29 Aug. 29, 2012, pp. 1-9.
Extended European Search Report, App. No. EP18790917.1, dated Apr. 8, 2021, 13 Pages.
MycoBank Database, retrieved online on Apr. 28, 2017, Internet<URL:http://www.mycobank.org/>, 4 Pages.
JBIF Japan Node of Global Biodiversity Information Facility, [retrieved online on Apr. 28, 2017, Internet <URL:http://www.gbif.jp/bol>, 2 Pages.
"BISMaL," retrieved online on Apr. 28, 2017, Internet<URL:http://www.godac.jamstec.go.jp/bismal/j/using.html>, 6 Pages.
Inoue, et al., "DNA barcoding of weevils from Aichi and neighboring prefectures centering on Nagoya City in Japan", Biodiversity in Nagoya, Mar. 2017,vol. 4, pp. 23-29, ISSN 2188-2541.
Shirayama, , "Census of marine life : its accomplishment and futureperspective", Global Environmental Research, vol. 16, No. 1, 2011, pp. 81-86.
Carstensen, et al., "7.08-Coastal Monitoring Programs", Treatise on Estuarineand Coastal Science, 2011, vol. 7, pp. 175-206.
International Search Report, App No. PCT/JP2018/017300, dated Jul. 17, 2018, 3 Pages.
Office Action Search Report, App. No. CN201880002968.4, dated Nov. 28, 2022, 15 Pages.
Search Report, App. No. JP201880002968.4, dated Nov. 28, 2022, 15 Pages.

* cited by examiner

FIG. 2

| TYPE INFORMATION | TIME AND DATE INFORMATION | SEA AREA INFORMATION | IMAGE | FIRST POPULATION INFORMATION |
|---|---|---|---|---|
| | | | | |
| | | | | |
| | | | | |
| | | | | |

FIG. 3

| TYPE INFORMATION | TIME AND DATE INFORMATION | SEA AREA INFORMATION | BASE SEQUENCE INFORMATION | SECOND POPULATION INFORMATION |
|---|---|---|---|---|
| | | | | |
| | | | | |
| | | | | |

FIG. 4

| TYPE INFORMATION | TIME AND DATE INFORMATION | SEA AREA INFORMATION | IMAGE | FIRST POPULATION INFORMATION | BASE SEQUENCE INFORMATION | SECOND POPULATION INFORMATION |
|---|---|---|---|---|---|---|
| | | | | | | |
| | | | | | | |
| | | | | | | |

INTEGRATION SYSTEM AND INTEGRATION METHOD

TECHNICAL FIELD

The present invention relates to a technique for a database of biological images and the like.

Priority is claimed on Japanese Patent Application No. 2017-090809, filed in Japan on Apr. 28, 2017, and PCT Application PCT/JP2018/017300, filed on Apr. 27, 2018, the content of which are both incorporated herein by reference.

BACKGROUND ART

In the related art, databases of information necessary for identifying and classifying organisms are being constructed. For example, there are databases as shown in Non-patent literatures 1 to 3. In these databases, information such as individual nucleotide sequence information obtained from organisms is registered and utilized.

In addition, in the technique disclosed in Non-patent literature 1, links to image data are registered in the database.

CITATION LIST

Non-Patent Literature

[Non-Patent Literature 1] "MycoBank Database". [online], [accessed Apr. 28, 2017], Internet <URL: http://www.mycobank.org/>
[Non-Patent Literature 2] "JBIF Global Biodiversity Information Organization Japan Nodes", [online], [accessed Apr. 28, 2017], Internet <URL: http://www.gbif.jp/bol>
[Non-Patent Literature 3] "BISMaL", [online], [accessed Apr. 28, 2017]], Internet <URL: http://www.godac.jamstec.go.jp/bismal/j/using.html>

SUMMARY OF INVENTION

Technical Problem

However, while it was possible to acquire the nucleotide sequence information of organisms individually in the related art, using the information was difficult.

In view of this, it is an object of the present invention to provide a database which has nucleotide sequence information and which is more easily used.

Solution to Problem

An aspect of the present invention is an integration system comprising a biological image acquiring device which acquires, from a sample including biological particles which are a detection target, a biological image which is an image of the biological particles, a nucleotide sequence information acquiring device which acquires nucleotide sequence information of the biological particles, and an integration device which associates and registers the biological image and the nucleotide sequence information acquired from the same type of biological particles in an integrated database.

An aspect of the present invention is the integration system described above, further comprising a biological information determination device which acquires information relating to a population for each type of the biological particles in the sample based on an image acquired by the biological image acquiring device, in which the integration device associates and registers the information relating to the population obtained based on the image in the integrated database in addition to the biological image and the nucleotide sequence information.

An aspect of the present invention is the integration system described above, further comprising a nucleotide sequence information determination device which acquires information relating to a population for each type of the biological particles in the sample based on nucleotide sequence information acquired by the nucleotide sequence information acquiring device, in which the integration device associates and registers the information relating to the population obtained based on the nucleotide sequence information in the integrated database in addition to the biological image and the nucleotide sequence information.

An aspect of the present invention is the integration system described above, in which, in a state in which a fluid including the sample flows in a flow cell, the biological image acquiring device acquires the biological image by imaging the fluid.

An aspect of the present invention is the integration system described above, further comprising a biological information determination device which acquires first individual information which is information relating to a population for each type of the biological particles in the sample based on an image acquired by the biological image acquiring device, and a nucleotide sequence information determination device which acquires second individual information which is information relating to a population for each type of the biological particles in the sample based on nucleotide sequence information acquired by the nucleotide sequence information acquiring device, in which the integration device associates and registers the image corresponding to the first individual information and the nucleotide sequence information corresponding to the second individual information in the integrated database when the first individual information and the second individual information are determined to be similar information based on predetermined criteria.

An aspect of the present invention is the integration system described above, further comprising an analysis device for identifying the nucleotide sequence information of the biological particles of a newly acquired biological image or identifying a biological image of nucleotide sequence information of a newly acquired organism based on association between the biological image and the nucleotide sequence information registered in the integrated database.

An aspect of the present invention is the integration system described above, in which the analysis device carries out identification further based on obtained attribute information relating to the biological particles.

An aspect of the present invention is the integration system described above, in which the integration device estimates a classification group of the biological particles based on the biological image or the nucleotide sequence information.

An aspect of the present invention is an integration method comprising a biological image acquiring step of acquiring, from a sample including biological particles which are a detection target, a biological image which is an image of the biological particles, a nucleotide sequence information acquiring step of acquiring nucleotide sequence information of the biological particles, and an integration step of associating and registering the biological image and the nucleotide sequence information acquired from the same type of biological particles in an integrated database.

Advantageous Effects of Invention

According to the present invention, it is easier to use a database having nucleotide sequence information.

BRIEF DESCRIPTION OF DRAWINGS

FIG. 2 is a diagram showing specific examples of information to be stored in an image database.

FIG. 3 is a diagram showing specific examples of information to be stored in a nucleotide sequence information database.

FIG. 4 is a diagram showing specific examples of information to be stored in an integrated database.

DESCRIPTION OF EMBODIMENTS

Figure 1:
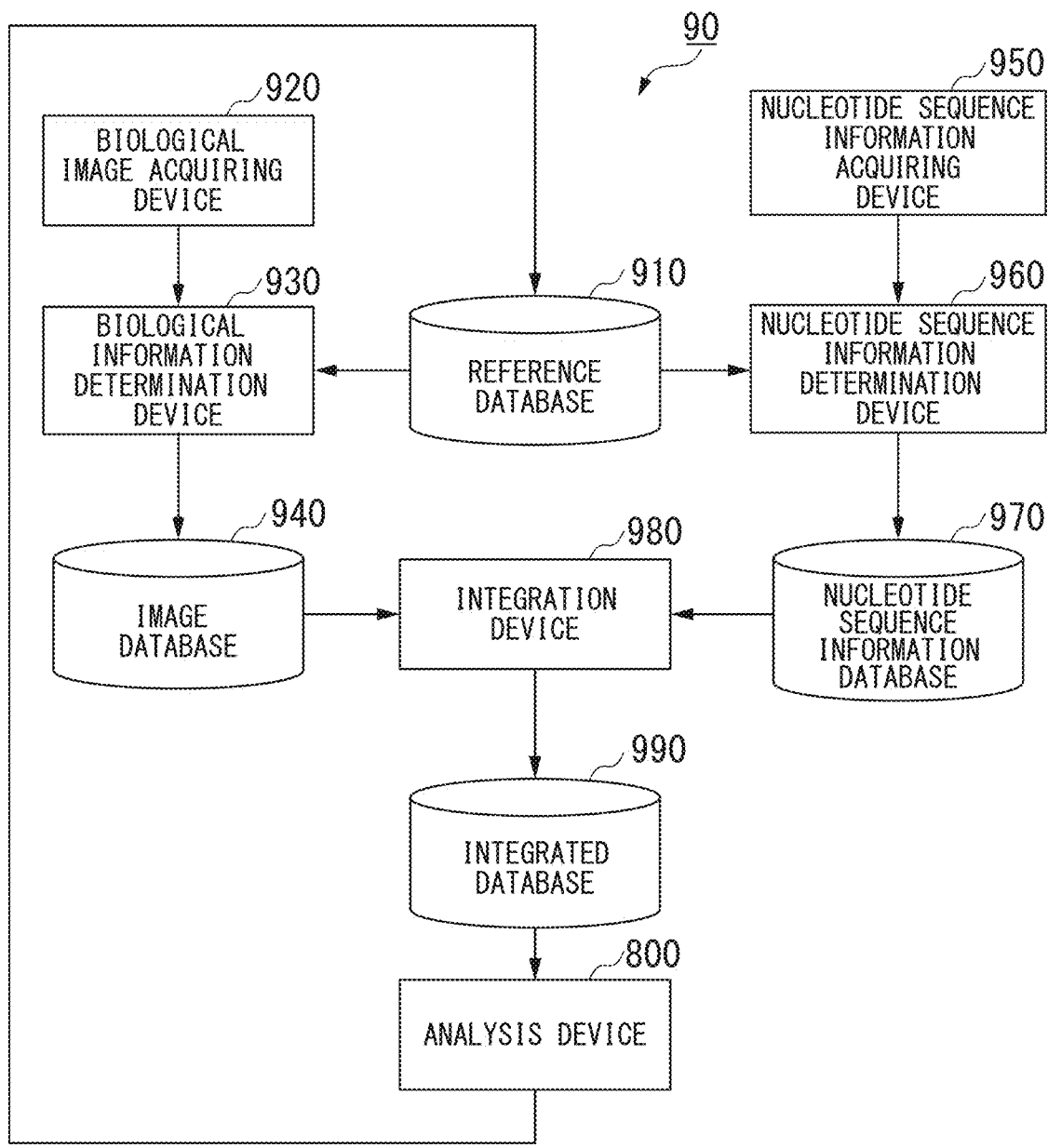
FIG. 1 schematically shows an integration system according to one embodiment of the present invention.

FIG. 1 is a diagram schematically illustrating the integration system 90 according to one embodiment of the present invention. A detailed description of the integration system 90 will be given below. The integration system 90 is provided with a reference database 910, a biological image acquiring device 920, a biological information determination device 930, an image database 940, a nucleotide sequence information acquiring device 950, a nucleotide sequence information determination device 960, a nucleotide sequence information database 970, an integration device 980, and an integrated database 990. In addition, an analysis device 800 performs an analysis process based on the data of the integrated database 990 generated by the integration system 90.

The reference database 910 is configured using a storage device such as a magnetic hard disk device or a semiconductor storage device. The reference database 910 stores reference data. The reference data includes image reference data and nucleotide sequence reference data.

The image reference data is data in which already known image information and type information are associated with each other. The image information included in the image reference data may be data of the image itself or data indicating a characteristic amount obtained from the image. Here, the characteristic amounts include morphological characteristics (images) for classification group identification. Using the image reference data makes it possible to determine what kind of organism image the image of the biological particles obtained from the sample is.

The nucleotide sequence reference data is data in which already known nucleotide sequence information and type information are associated with each other. The nucleotide sequence information included in the nucleotide sequence reference data may be information indicating the nucleotide sequence itself or may be data indicating a characteristic amount obtained from the nucleotide sequence. As the characteristic amount, metadata used in a database such as GenBank may be used. Using the nucleotide sequence reference data makes it possible to determine what type of organism nucleotide sequence information the nucleotide sequence information of the biological particle obtained from the sample is.

The biological image acquiring device 920 acquires a biological image of biological particles from a sample including biological particles which are a detection target. The biological image acquiring device 920 may acquire biological images by any means. For example, a biological image may be acquired by imaging a fluid in a state in which a fluid including a sample flows in the flow cell. A description of a specific example of the biological image acquiring device 920 will be given below.

For the biological images acquired by the biological image acquiring device 920, the biological information determination device 930 determines what type of organisms the biological particles of the biological image are. The biological information determination device 930 may determine the type of organism based on the acquired biological image and the image reference data stored in the reference database 910, for example. The biological information determination device 930 associates and registers the type information (information indicating the type of organism) as the determination result and the image, in the image database 940. In the present embodiment, the biological information determination device 930 further associates and registers date and time information indicating the date and time when the sample was collected, sea area information indicating the sea area where the sample was collected, and first population information relating to the population of that type of organism. For the determination of the acquired image data and the image of the reference database 910, for example, the shape and the characteristics of the organism used in image recognition techniques, or the relationships, the distances, the sizes, the colors, and the like of the characteristic shapes may be used. The relationships of the characteristic shapes indicate relationships between the positional relationship and orientation of a plurality of characteristically shaped portions. The distances indicate distances between a plurality of distinctive shapes.

The first population information is acquired by the biological information determination device 930 based on the image. For example, the biological information determination device 930 may acquire the population of biological particles detected from the sample which is the treatment target for each type of biological particle. The biological information determination device 930 may acquire the population for each type acquired in this manner as the first population information. As first population information, the biological information determination device 930 may acquire a value (for example, a percentage value) indicating the ratio (appearance ratio) of the population of each type with respect to the population of all types of biological particles detected from the sample which is the treatment target.

The image database 940 is configured using a storage device such as a magnetic hard disk device or a semiconductor storage device. The image database 940 stores the information acquired by the biological information determination device 930 as a database. FIG. 2 is a diagram showing specific examples of information to be stored in the image database 940. The image database 940 stores a table having values of each of type information, date and time information, sea area information, images, and first population information. The image registered in the table of the image database 940 is not necessarily an image of all the detected individuals, but may be a representative image among a plurality of biological images obtained from the same type of biological particle. Which image is selected as the representative image may be determined based on the kind of determination criteria. For example, an image considered to be most clear to the human eye may be selected as a representative image. For example, an image of the largest body part of the living organism may be selected as the representative image. Such a treatment may be executed by the biological information determination device 930, for example.

The nucleotide sequence information acquiring device 950 acquires nucleotide sequence information of biological particles from a sample including biological particles which are a detection target. The nucleotide sequence information acquiring device 950 may acquire the nucleotide sequence information by any means. For example, nucleotide sequence information may be acquired by performing DNA extraction, polymerase chain reaction (PCR), and sequence analysis on a sample. For example, nucleotide sequence information may be acquired by large-scale nucleotide sequencing analysis using a next generation sequencer (for example, a nucleotide sequence analysis method known as metagenome analysis or the like). In such a case, for example, it is also possible to use a technique known as metabarcoding (DNA Barcoding) or amplicon analysis for analyzing an amplified product of a nucleotide sequence fragment which identifies a classification group using the PCR method, or to use a nucleotide sequence known as a shotgun sequence, which is derived from the mixed nucleic acid of the biological species in a sample. A DNA or reverse transcript RNA (cDNA) may be the nucleic acid used for nucleotide sequence analysis.

The sample which is the treatment target of the nucleotide sequence information acquiring device 950 is the same sample as the sample which is the treatment target of the biological image acquiring device 920. That is, images and nucleotide sequence information are acquired for the same sample. Although not mandatory, for the order of processing, the biological image acquiring device 920 may acquire the image first, and then the nucleotide sequence information acquiring device 950 may acquire the nucleotide sequence information relating to the target sample. In order to acquire a more direct sample image and nucleotide sequence, DNA analysis may be performed on a sample (sample which was performed image acquisition and recovered for DNA analysis) treated in this order The nucleotide sequence information determination device 960 determines what type of organisms the biological particles of the nucleotide sequence information are, for the nucleotide sequence information acquired by the nucleotide sequence information acquiring device 950. Such a determination may be realized, for example, by performing a homology search. Such a determination is preferably made based on nucleotide sequence information of a portion having high preservability in each organism in the nucleotide sequence information, for example. For example, for eukaryotes, 18S ribosomal RNA gene sequence may be used for the determination.

The nucleotide sequence information determination device 960 may determine the type of organism based on the acquired nucleotide sequence information and the nucleotide sequence reference data stored in the reference database 910, for example. The nucleotide sequence information determination device 960 associates and registers the type information, which is the determination result, and the nucleotide sequence information, in the nucleotide sequence information database 970. In the present embodiment, the nucleotide sequence information determination device 960 associates and registers date/time information indicating the date and time when the sample was taken, sea area information indicating the sea area where the sample was sampled, and second population information relating to the number of organisms of that type.

The second population information is acquired by the nucleotide sequence information determination device 960 based on the nucleotide sequence information. For example, the nucleotide sequence information determination device 960 may acquire the population of biological particles detected from the sample which is the treatment target for each type of biological particle based on the number of reads (the number of acquired sequences). The nucleotide sequence information determination device 960 may acquire the population of each type acquired in this manner as second population information. The nucleotide sequence information determination device 960 may acquire a value (for example, a percentage value) indicating a ratio (appearance ratio) of the population of each type with respect to the populations of all types of biological particles detected from the sample which is the treatment target, as second population information.

The nucleotide sequence information database 970 is configured using a storage device such as a magnetic hard disk device or a semiconductor storage device. The nucleotide sequence information database 970 stores the information acquired by the nucleotide sequence information determination device 960 as a database. FIG. 3 is a diagram showing specific examples of information to be stored in the nucleotide sequence information database 970. The nucleotide sequence information database 970 stores a table having values of type information, date and time information, sea area information, nucleotide sequence information, and second population information. The nucleotide sequence information registered in the table of the nucleotide sequence information database 970 does not need to be the nucleotide sequence information of all the detected individuals, but may be representative nucleotide sequence information from among a plurality of items of nucleotide sequence information obtained from the same type of biological particle. What kind of nucleotide sequence information is selected as the representative nucleotide sequence information may be determined based on any kind of determination criteria. For example, the nucleotide sequence information considered to be most representative may be arbitrarily selected as representative nucleotide sequence information. For example, nucleotide sequence information whose characteristic amount is closest to the average value may be selected as representative nucleotide sequence information. Such a treatment may be executed by the nucleotide sequence information determination device 960, for example.

The integration device 980 integrates the information of the image database 940 and the information of the nucleotide sequence information database 970 to generate an integrated database. At this time, the integration device 980 integrates each database using the type information in the image database 940 and the type information in the nucleotide sequence information database 970 as keys. That is, the integration device 980 integrates the database by combining records having the same type information with respect to the records of the image database 940 and the records of the nucleotide sequence information database 970. In the integration of the information in the image database 940 and the information in the nucleotide sequence information database 970 in the integration device 980, information relating to the population of the sample organism, distribution, or type information, or classification information may be determined for the integration, using AI techniques such as deep learning used in so-called big data.

The integrated database 990 is configured using a storage device such as a magnetic hard disk device or a semiconductor storage device. The integrated database 990 stores the integrated database integrated by the integration device 980. FIG. 4 is a diagram showing a specific example of information to be stored in the integrated database 990. The integrated database 990 stores a table having each of the values of type information, date and time information, sea area information, images, first population information, nucleotide sequence information, and second population information.

The analysis device 800 executes an analysis process based on the information registered in the integrated database 990. The analysis process executed by the analysis device 800 may be any process. A description of a specific example of the analysis process executed by the analysis device 800 will be given below. For example, the analysis device 800 may acquire nucleotide sequence information based on images of biological particles acquired from a new sample. It is possible to more easily execute such a process by using the integrated database 990 in which the image information and the nucleotide sequence information are integrated. For example, the analysis device 800 may acquire biological images based on the nucleotide sequence information of the biological particles acquired from the new sample. It is possible to more easily execute such a process by using the integrated database 990 in which the image information and the nucleotide sequence information are integrated.

The analysis device 800 may estimate the population of organisms obtained from a new sample by using the individual information obtained from the integrated database 990 based on the nucleotide sequence information of the organism. It is possible to easily execute such a process by using the integrated database 990. The analysis device 800 may determine if any sea areas which are similar with respect to the ratio of the population of each type in the sea area which is the treatment target are present in other sea areas. In a case where similar sea areas are present, it is also possible to determine whether there are a plurality of similar environments and whether preservation is possible in another location if the balance of the organisms is destroyed in one location.

The analysis device 800 may determine a kind of organism and what kind of growth state the organism is in based on the biological particle image and nucleotide sequence information obtained from the new sample. Such a process is useful for a case where it is difficult to determine the type and growth state of an organism by using either the image or the nucleotide sequence information alone. For example, nauplius larvae have a similar appearance in a plurality of types of organisms. Therefore, it is difficult to carry out the determination only with images. On the other hand, since the nucleotide sequence information of nauplius larvae differs for each type of organism, it is possible to determine the type of the organism. However, it is difficult to determine the growth state based on the nucleotide sequence information. Therefore, it is difficult to determine whether an organism is a nauplius larva or an adult based only on the nucleotide sequence information. In response to such a problem, since the analysis device 800 described above carries out determination based on biological particle images and nucleotide sequence information, it is possible to determine whether an organism is a nauplius larva or an adult based on the images and to determine the type of organism based on the nucleotide sequence information. As a result, it is possible to determine the type and growth state of the organism with high accuracy.

The analysis device 800 may update the contents of the reference database 910 based on the data registered in the integrated database 990. For example, the images and the characteristic amounts of the image reference data may be updated based on the images and the type information registered in the integrated database 990. For example, the nucleotide sequence information and the characteristic amount of the nucleotide sequence information reference data may be updated based on the nucleotide sequence information and the type information registered in the integrated database 990.

According to the integration system 90 configured in this manner, database utilization becomes easier with the database having the nucleotide sequence information. Specifically, as in the analysis device 800 described above, it is possible to more easily execute analysis processes which were difficult or laborious to execute in databases of the past.

In addition, in the integration system 90, the integrated database 990 in which biological images and nucleotide sequence information are associated with each other for the same sample is constructed. In the related art, it was difficult to associate and register the acquired organism image with the nucleotide sequence obtained from the organism appearing in the image in the database. However, as described above, in the integration system 90, it is possible to associate and register biological images and nucleotide sequence information obtained from the same sample.

Here, a part or all of the biological information determination device 930, the nucleotide sequence information determination device 960, the integration device 980, and the analysis device 800 may be implemented by a program executed by an information processing apparatus provided with a central processing unit (CPU), a memory, or the like, or may be realized by using hardware such as ASIC.

First Modified Example

In the embodiment described above, images and nucleotide sequence information are registered in the reference database 910 in advance for biological particles which are a detection target. Next, a description of the operation of the integration system 90 in a case where biological particles for which images and nucleotide sequence information are not registered in the reference database 910 are present in the sample will be given.

It is not possible for the biological information determination device 930 to determine the type of biological particles with respect to the biological image acquired by the biological image acquiring device 920. The biological information determination device 930 acquires information (first population information) relating to the population of biological particles having a similar image with respect to the image of the biological particles which are a detection target. The biological information determination device 930 registers the information relating to the image and the first individual information in the image database 940 for the image of the biological particles for which it is not possible to determine the type. In addition, in a case where the biological image acquired by the biological image acquiring device 920 does not match any of the images registered in the reference database 910, the biological information determination device 930 registers an unconfirmed identifier as the type information. As described above, the unconfirmed identifier is information indicating that there is no match with any image registered in the reference database 910.

It is not possible for the nucleotide sequence information determination device 960 to determine the type of biological particles with respect to the nucleotide sequence information acquired by the nucleotide sequence information acquiring device 950. The nucleotide sequence information determination device 960 acquires information (second population information) relating to the population of biological particles having similar nucleotide sequence information with respect to the nucleotide sequence information of biological particles which are a detection target. The nucleotide sequence information determination device 960 registers the nucleotide sequence information and the second individual information in the nucleotide sequence information database 970 with respect to the nucleotide sequence information of the biological particles for which it is not possible to determine the type. In addition, in a case where the nucleotide sequence information acquired by the nucleotide sequence information acquiring device 950 does not match any of the nucleotide sequence information registered in the reference database 910, the nucleotide sequence information determination device 960 registers an unconfirmed identifier as the type information. The unconfirmed identifier is information indicating that there is no match with any of the nucleotide sequence information registered in the reference database 910 as described above. At this time, the nucleotide sequence information determination device 960 may further register homology information in association with the unconfirmed identifier. Homology information is information relating to the result of a homology search. The homology information is, for example, information relating to the value of the homology rate showing the highest value and information relating to the name of the organism with the highest homology. For example, a genus name and a species name may be used as the information relating to the name. In a case where a plurality of organisms exhibiting the highest level of homology are found by searching, a plurality of pieces of information may all be registered.

The integration device 980 integrates the information of the image database 940 and the information of the nucleotide sequence information database 970 to generate an integrated database. In the process relating to the biological particles for which information is not registered in the reference database 910 as in the present specification, the integration device 980 integrates each database using the first individual information in the image database 940 and the second individual information in the nucleotide sequence information database 970 as keys. That is, the integration device 980 integrates the database by combining the records in which the first individual information and the second individual information are similar, with respect to the records of the image database 940 and the records of the nucleotide sequence information database 970. For example, in a case where both the first individual information and the second individual information indicate the ratio to the population of all types of biological particles, the records with the smallest difference in ratio value may be combined with each other. In other words, the fact that the first individual information and the second individual information are similar signifies that images and nucleotide sequence information of approximately the same population were acquired in the sample.

Figure 5:
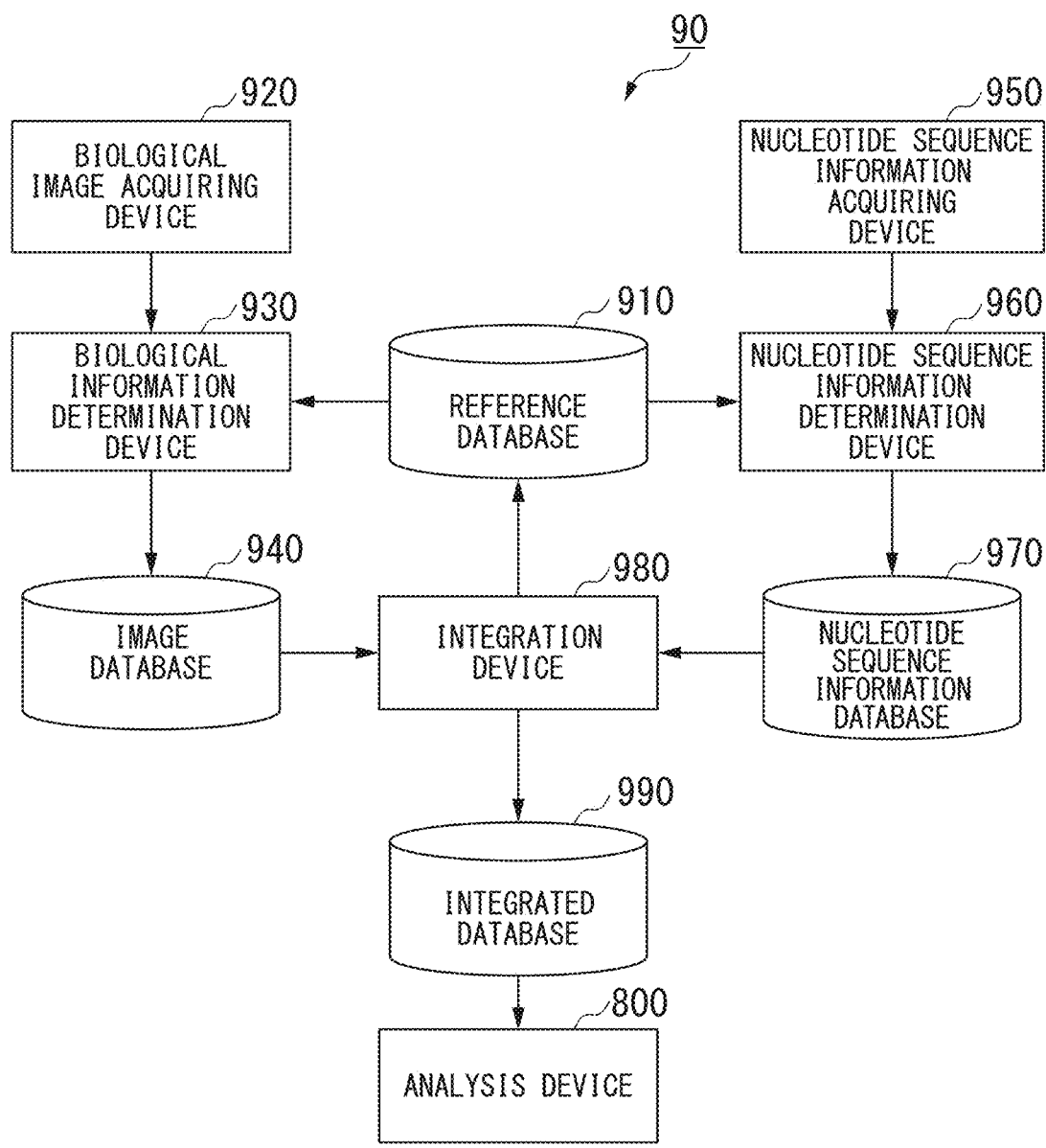
FIG. 5 is a diagram schematically showing an integration system 90 in a first modified example.

Therefore, even for biological particles which are not registered in the reference database 910, it is possible to associate images and nucleotide sequence information of the same biological type with high precision based on the population. Records registered in the integrated database 990 by the integration device 980 may be additionally registered in the reference database 910. FIG. 5 is a diagram showing an outline of the integration system 90 in the first modified example configured to perform the additional registration in this manner. With such a configuration, in the processes of the subsequent biological information determination device 930, the nucleotide sequence information determination device 960, and the like, it is possible to carry out identification using the reference database 910 even for biological particles for which identification was not possible up to that point.

The integration device 980 may perform a classification group estimation process for records in which unconfirmed identifiers are registered as the type information. A description of the classification group estimation process will be given below. The integration device 980 may estimate the classification group based on the homology information registered in association with the unconfirmed identifier. For example, the integration device 980 may estimate that the organism of the record in which the unconfirmed identifier is registered is an organism of a classification group close to an organism registered as homology information. The integration device 980 may create a phylogenetic tree using the searched sequence for the organisms of the record in which unconfirmed identifiers are registered and estimate the classification group from the result. The integration device 980 may estimate the classification group based on the homology information and the phylogenetic tree. More specifically, in a case where a plurality of classification groups are estimated when carrying out estimation based on the homology information, the integration device 980 may create a phylogenetic tree using the searched sequence, and the classification group may be estimated based on the result. In addition, in a case where the result estimated based on the homology information is different from the result estimated based on the phylogenetic tree, the integration device 980 may give priority to the estimation result based on one predetermined phylogenetic tree. In a case where the image and the nucleotide sequence information are associated for the record in which the unconfirmed identifier is registered by the above-described process, the classification group estimation process may be further performed based on this image. For example, in a case where a plurality of classification groups are estimated, image analysis may be performed on representative images (images registered in the reference database 910) in each classification group and images of unconfirmed identifiers, and the classification group of images having closer characteristics may be obtained as the estimation result. With respect to the record in which the unconfirmed identifier is registered, the integration device 980 may associate the biological image with the nucleotide sequence information as follows. First, the integration device 980 estimates a classification group based on homology information and/or a phylogenetic tree obtained in relation to nucleotide sequence information. The integration device 980 selects a biological image from the records in which unconfirmed identifiers are registered based on the classification group obtained as the estimation result. As specific examples of the method by which the integration device 980 selects a biological image, there are the following two methods. However, there is no need to limit the method to the two methods shown below. (1) Acquire a biological image of a record having related type information from the image database 940 based on type information such as scientific names included in the classification group. (2) Search for images of organisms from existing data such as articles and books based on classification information such as scientific names included in the classification group, and acquire biological images similar to images obtained as search results from records. The estimation result of the classification group obtained in this manner may be additionally registered in the reference database 910 by the process described above.

Second Modified Example

In the embodiment described above, for the biological particles which are a detection target, images and nucleotide sequence information are registered in advance in the reference database 910, or neither images nor nucleotide sequence information are registered. Next, there may be cases in which biological particles for which one of images or nucleotide sequence information is registered in the reference database 910 and the other is not registered are present in the sample. As a specific example, a description of a case where an image is registered in the reference database 910 and nucleotide sequence information is not registered will be given.

It is possible for the biological information determination device 930 to determine the type of biological particles with respect to the biological image acquired by the biological image acquiring device 920. For the biological images acquired by the biological image acquiring device 920, the biological information determination device 930 determines what type of organisms the biological particles of the biological image are. The biological information determination device 930 associates and registers the type information which is the determination result (information indicating the type of organism), the image, and the first population information relating to the population of that type of organism in the image database 940.

It is not possible for the nucleotide sequence information determination device 960 to determine the type of biological particles with respect to the nucleotide sequence information acquired by the nucleotide sequence information acquiring device 950. The nucleotide sequence information determination device 960 acquires information (second population information) relating to the population of biological particles having similar nucleotide sequence information with respect to the nucleotide sequence information of biological particles which are a detection target. The nucleotide sequence information determination device 960 registers the nucleotide sequence information and the second individual information in the nucleotide sequence information database 970 with respect to the nucleotide sequence information of the biological particles for which it is not possible to determine the type.

The integration device 980 integrates the information of the image database 940 and the information of the nucleotide sequence information database 970 to generate an integrated database. In the process relating to the biological particles in which information of either one of the image and the nucleotide sequence information is not registered in the reference database 910 as described above, the integration device 980 integrates each database with the first individual information in the image database 940 and the second individual information in the nucleotide sequence information database 970 as keys. That is, the integration device 980 integrates the database by combining the records in which the first individual information and the second individual information are similar, with respect to the records of the image database 940 and the records of the nucleotide sequence information database 970. For example, in a case where both the first individual information and the second individual information indicate the ratio to the population of all types of biological particles, the records with the smallest difference in ratio value may be combined with each other. In other words, the fact that the first individual information and the second individual information are similar signifies that images and nucleotide sequence information of approximately the same population were acquired in the sample. Therefore, even for biological particles for which either one of images and nucleotide sequence information are unregistered in the reference database 910, it is possible to associate images of the same type of biological type and nucleotide sequence information with high precision based on the population. Records registered in the integrated database 990 by the integration device 980 may be additionally registered in the reference database 910. In a case where the information relating to the type identification is stored in the nucleotide sequence information, the shape and characteristics of the organism are estimated from the information stored in the reference database 910 to confirm and integrate the target image output from the image database 940. In a case where information relating to the type identification is stored in the image, the nucleotide sequence information output from the nucleotide sequence information database 970 may be confirmed and integrated by estimating a characteristic nucleotide sequence from the characteristic amounts (morphological characteristics (images) for classification group identification) stored in the reference database 910. In addition, in a case where the information relating to the type identification is stored in the nucleotide sequence information, the target image output from the image database 940 may be confirmed and integrated by estimating the shape and characteristics of the organism from the information stored in the reference database 910.

Third Modified Example

In the first modified example or the second modified example described above, a reverse transcription of RNA (cDNA) may be the nucleic acid used for nucleotide sequence analysis. With such a configuration, there is a possibility of including a nucleotide sequence which is not present (which lived in the past) in the DNA, while a biological image obtained from the biological image acquiring device 920 has a target which is currently present (which is alive). Therefore, on the basis of the second individual information (ecological number and distribution) based on the nucleotide sequence information of the RNA targeting organisms which are present, it becomes possible to carry out integration more efficiently with the first individual information based on the image. In addition, the use of RNA also has an advantage in that introns (sequences not used for transcription) are not included in eukaryotes. Not including introns in this manner makes it possible to more reliably acquire the gene nucleotide sequence to be analyzed.

Fourth Modified Example

In a case where the size of the biological particles which are a detection target is detected, the biological information determination device 930 may determine the type of the organism based on the acquired biological image and information relating to the size of the biological particle. In such a case, it is desirable for the reference database 910 to include information relating to the size of the organism of the image with respect to the image reference data. With such a configuration, even for organisms with similar appearances, if the organisms have different sizes, it is possible to make determinations with higher precision in the biological information determination device 930. It is possible to obtain information relating to the size of biological particles which are a detection target using a sieving device 110 described below, for example. That is, it is possible to use information indicating which of a plurality of sieves was passed through and which sieve was not passed through, as information relating to the size.

The process of determining the type of organism using the information relating to the size of the biological particles may be used in the nucleotide sequence information determination device 960. That is, the nucleotide sequence information determination device 960 may determine the type of the organism based on the acquired nucleotide sequence information and information relating to the size of the biological particle.

As described above, the process of determining the type of organism using the information relating to the size of the biological particle may be used in the analysis device 800. For example, the analysis device 800 may determine the type of organism based on the image of the biological particles acquired from the new sample and the information relating to the size of the biological particles. In such a case, the integrated database 990 has information relating to the size of biological particles. For example, the analysis device 800 may determine the type of organism based on the nucleotide sequence information of the biological particles acquired from the new sample and the information relating to the size of the biological particles. For example, the analysis device 800 may determine the type of organism based on the image of the biological particle acquired from the new sample, the nucleotide sequence information of the biological particles, and the information relating to the size of the biological particles.

Fifth Modified Example

The biological information determination device 930 may determine the type of organism based on the acquired biological image and information relating to the location where the sample which is a detection target was collected. The information relating to the location where the sample was collected may be information indicating the sea area from which the sample was collected, may be information indicating the depth of the sea from which the sample was collected, or may be both. In such a case, it is desirable for the reference database 910 to include information relating to the location where the organisms of the image are living with respect to the image reference data. With such a configuration, even for organisms with similar appearances, it is possible to make determinations with higher precision in the biological information determination device 930 if the organisms live in different locations.

In addition, although the biological information determination device 930 obtains the determination result of the type of organism as a highly reliable determination result based on the acquired biological image, in a case where the information relating to the location where the sample was collected does not match the contents of the reference database 910, information relating to the location where the sample was collected may be output as a candidate for a new habitat of the detected organism. With such a configuration, it is possible to find a location which was not recognized as a habitat as a new habitat.

The process of determining the type of organism using the information relating to the location where the sample is collected may be used in the nucleotide sequence information determination device 960. That is, the nucleotide sequence information determination device 960 may determine the type of organism based on the acquired nucleotide sequence information and information relating to the location where the sample was collected.

The process of determining the type of organism using the information relating to the location where the sample is collected may be used in the analysis device 800. For example, the analysis device 800 may determine the type of organism based on the image of the biological particle acquired from the new sample and the information relating to the location where the sample was sampled. In such a case, the integrated database 990 has information relating to the habitat of biological particles. For example, the analysis device 800 may determine the type of organism based on the nucleotide sequence information of the biological particle acquired from the new sample and the information relating to the location where the sample was collected. For example, the analysis device 800 may determine the type of the organism based on the image of the biological particles acquired from the new sample, the nucleotide sequence information of the biological particle, and the information relating to the location where the sample was collected.

Here, the information relating to the size of the biological particles and the information relating to the location where the sample was collected shown as the fourth and fifth modified examples are merely specific examples of attribute information relating to the organisms (referred to below as "meta information"). The meta information may be any information as long as it is information relating to the organism which is a detection target. Any information may be used as the meta information relating to the organism. For example, information relating to the color of the appearance of organisms, information relating to the timing of the activity of the organisms, and information relating to the things eaten by the organisms may be used as the meta information for determination in the same manner.

Sixth Modified Example

Any apparatus may be implemented as the apparatus provided with the analysis device 800. For example, the analysis device 800 may be implemented in a general-purpose information processing apparatus such as a mobile phone, a smartphone, or a personal computer. Such an implementation may be implemented, for example, as a distributable application program. In this case, the information processing apparatus in which the application program is installed may acquire information or the like relating to the type of organism according to the images or nucleotide sequence information acquired from the sample by acquiring the information of the integrated database 990 implemented in the server according to the operation of the user.

In addition, such an implementation may be implemented as an application program for providing the user with an interface to the analysis device 800 implemented in the server. In this case, the information processing apparatus in which the application program is installed may acquire information or the like relating to the type of organism by asking the analysis device 800 of the server for the image and the nucleotide sequence information acquired from the sample according to the operation of the user.

A detailed description of a specific example of the biological image acquiring device 920 will be given below.
<Method of Pretreating Sample Including Biological Particles>

First Embodiment

In one embodiment, the present invention relates to a method of pretreating a sample including biological particles, the method including a step of acquiring a fraction (1*b*) which passes through a sieve (A) having meshes of 250 to 1000 µm and does not pass through a sieve (B) having meshes of 32 to 63 µm by sieving a sample including biological particles as a detection target (hereinafter referred to as "step (I)"), and a step of adding a colloidal solution having a density of 1.10 to 2.45 g/cm$^3$ to the fraction (1*b*), subjecting the resultant solution to centrifugation, and acquiring a supernatant fraction (S0) after the centrifugation (hereinafter referred to as "step (II)").

A description will be given of an outline of the method of the present embodiment with reference to FIGS. 1*a* to 1*c*.

Figure 6:
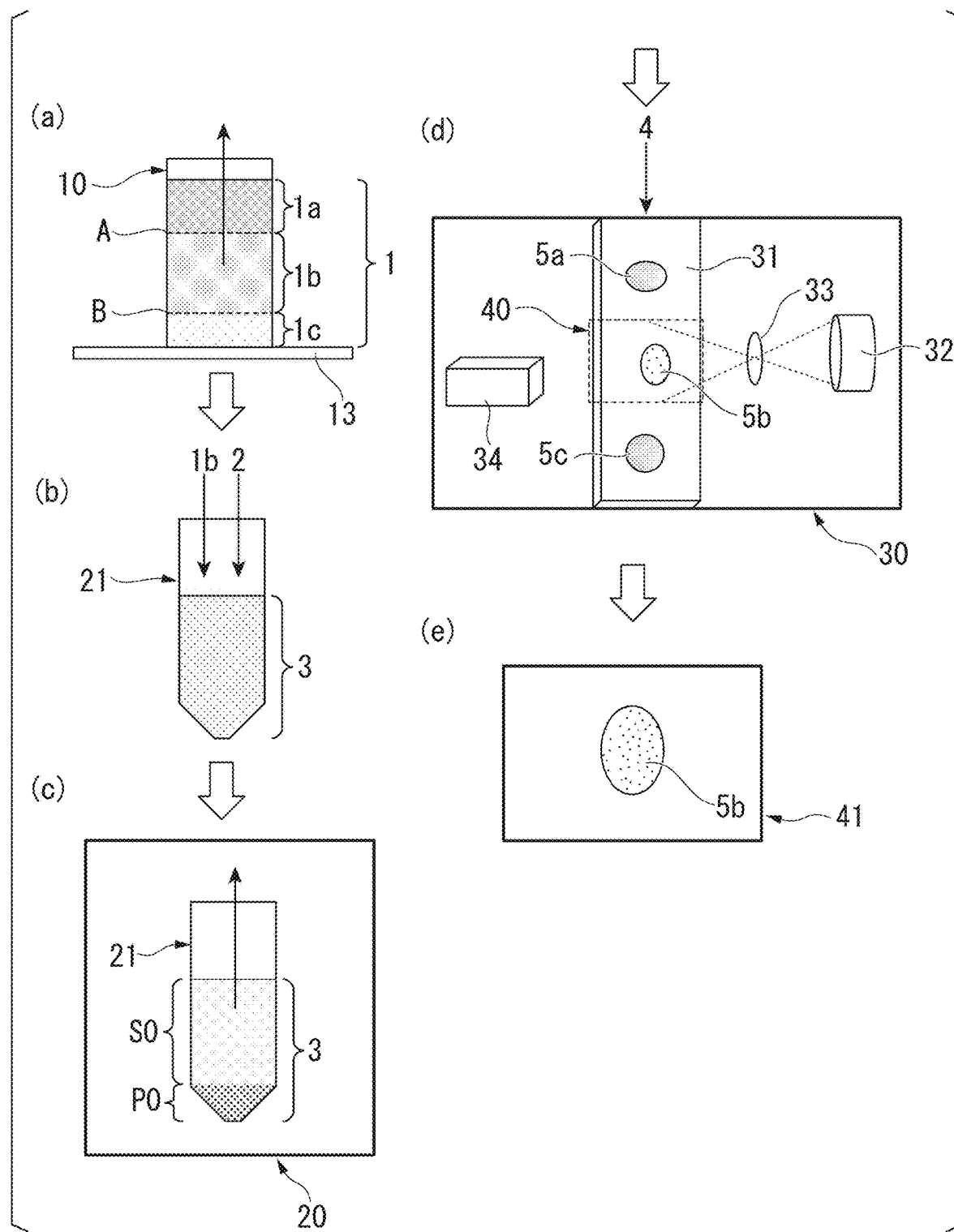
FIG. 6 shows an outline of a biological particle image acquiring method according to one embodiment of the present invention.

First, a sample 1 including biological particles as a detection target is sieved using a sieve (A) having meshes of 250 to 1000 µm and a sieve (B) having meshes of 32 to 63 µm, and a fraction (1*b*) which passes through the sieve (A) and does not pass through the sieve (B) is acquired (FIG. 6*a*; step (I)).

Next, a colloidal solution 2 having a density of 1.10 to 2.45 g/cm$^3$ is added to the fraction (1*b*) and stirred appropriately (FIG. 6*b*). Thereafter, a mixture 3 including the fraction (1*b*) and the colloidal solution 2 is subjected to centrifugation to acquire a supernatant fraction (S0) (FIG. 6*c*) (the above is step (II)).

A description will be given below of each step of the method of the present embodiment.
(Step (I))

Step (I) is a step of acquiring a fraction (1*b*) which passes through a sieve (A) having meshes of 250 to 1000 µm and does not pass through a sieve (B) having meshes of 32 to 63 µm by sieving a sample including biological particles as a detection target.

In step (I), the sample 1 including biological particles as a detection target is sieved. In the method of the present embodiment, the biological particles to be a detection target are biological particles which pass through a sieve (A) having meshes of 250 to 1000 µm and do not pass through a sieve (B) having meshes of 32 to 63 µm. Examples of such biological particles include meiofauna. The biological particles to be a detection target may be particles which pass through a sieve having meshes of 250 to 500 µm and do not pass through a sieve having meshes of 32 to 63 µm, or may be particles which pass through a sieve having meshes of 250 µm and do not pass through a sieve having meshes of 63 µm.

According to the method of the present embodiment, it is possible to acquire images having sufficient image quality to classify the organism species, even with a sample including a lot of sediment. Therefore, the biological particles to be a detection target may be organisms inhabiting the sediment. Examples of such organisms include benthic organisms or the like which live on the seafloor, lake bottoms, river bottoms, and the like. From this viewpoint also, meiofauna, which are benthic organisms, are suitable as the biological particles as a detection target.

The biological particles as a detection target for the method of the present embodiment may be the whole organism or a part of the organism. In addition, the biological particles may be dormant particles such as spores, eggs, and the like. In addition, the biological particles are not limited to living organisms, and may be dead organisms.

The sample 1 to be sieved according to the method of the present embodiment is not particularly limited as long as the sample 1 includes biological particles as a detection target. Examples of the sample 1 include samples or the like collected from an environment in which the biological particles as a detection target inhabit. In the method of the present embodiment, since the sample may include sediment, a sediment sample collected from the ocean floor, a lake bottom, a river bottom, or the like may be used as the sample 1. For example, in a case where the biological particles as a detection target are meiofauna, it is possible to use a sediment sample collected from the deep seafloor as the sample 1.

The sample 1 to be sieved according to the method of the present embodiment may be a sample collected from the environment as it is, or may be subjected to treatment such as fixation or dyeing. In a case where fixation of a sample is performed, it is possible to prevent decay of the sample. Therefore, it is preferable to fix the samples in a case where the collected samples are not to be used immediately. The fixation method is not particularly limited, and the fixation of the sample may be performed by a generally used method. For example, it is possible to fix using reagents such as formalin, ethanol, Lugol's solution, glutaraldehyde, RNAlater™ (Invitrogen), or the like, or by freezing. Examples of a suitable fixation method include formalin fixation.

In addition, in a case where the sample is subjected to a dyeing treatment, and then, an image of the biological particles in the pretreatment sample is acquired, it is possible to easily view the biological particles in the image. Therefore, the biological particles in the sample 1 are preferably dyed with a pigment or the like before sieving. The dyeing treatment method is not particularly limited, and the dyeing treatment for the sample may be performed using commonly used pigments or the like. For example, it is possible to perform the dyeing treatment using Rose Bengal, Congo Red, CellTracker™ Green (ThermoFisher Scientific), or the like. Examples of suitable dyeing treatment methods include Rose Bengal dyeing.

At least two sieves are used for sieving the sample 1. One is a sieve (A) having meshes of 250 to 1000 µm and the other is a sieve (B) having meshes of 32 to 63 µm. The sieve (A) having meshes of 250 to 1000 µm is used to remove fractions which do not pass through the sieve from the sample 1. In addition, a sieve (B) having meshes of 32 to 63 µm is used to remove the fraction which passes through the sieve from the sample 1. Then, in step (I), from the sample 1, a fraction which passes through the sieve (A) having meshes of 250 to 1000 µm and does not pass through a sieve (B) having meshes of 32 to 63 µm is acquired. Due to this, it is possible to remove sediment having a large diameter included in the sample 1 and to remove particles smaller than the biological particles as a detection target.

The sieves (A) and (B) are not particularly limited as long as the meshes are in the above ranges and commonly used sieves may be used. In addition, the size of the meshes may be varied within the above ranges according to the size of the biological particles as a detection target. Narrowing the range of meshes of the fraction (1b) acquired by sieving makes it possible to more efficiently image the biological particles as a detection target in a subsequent imaging step.

For example, in a case where the biological particles as a detection target are meiofauna, approximately 98% or more of the individuals are present in the sieve fraction of 38 to 500 μm, approximately 83% or more of the individuals are present in the sieve fraction of 38 to 250 μm, and approximately 75% of the individuals are present in the sieve fraction of 63 to 250 μm (refer to Table 1). Therefore, in step (I), a fraction which passes through a sieve of 250 to 500 μm and does not pass through a sieve of 32 to 63 μm may be acquired, a fraction which passes through a sieve of 250 to 500 μm and does not pass through a sieve of 38 to 63 μm may be acquired, and a fraction which passes through a 250 μm sieve and does not pass through a 63 μm sieve may be acquired.

The method of sieving in this step is not particularly limited and the sieving may be performed using a generally used method. For example, as shown in FIG. 6a, the sieve (A) having meshes of 250 to 1000 μm and the sieve (B) having meshes of 32 to 63 μm are installed in a container 10, and the sample 1 may be sieved by being poured over the sieve (A). Due to this, the sample 1 is sieved into a fraction (1a) which does not pass through the sieve (A) having meshes of 250 to 1000 μm, a fraction (1b) which passes through the sieve (A) having meshes of 250 to 1000 μm and does not pass through the sieve (B) having meshes of 32 to 63 μm, and a fraction (1c) which passes through the sieve (B) having meshes of 32 to 63 μm.

In the example shown in FIG. 6a, the container 10 is installed on a shaker 13 and sieving is performed while shaking with the shaker 13. Sieving while shaking makes it possible to shorten the time required for sieving.

After sieving, for example, it is possible to acquire the fraction (1b) by removing the sieve (A) including the particles trapped by the sieve (A) and obtaining the sieve (B) including the particles trapped by the sieve (B).

In the example of FIG. 6a, the sieve (A) and the sieve (B) are installed in the container 10, but the method of installing the sieve (A) and the sieve (B) is not limited thereto. For example, a container for gathering a fraction (1a) which does not pass through a sieve (A), a container for gathering a fraction (1b) which passes through the sieve (A) and does not pass through the sieve (B), a container for gathering a fraction (1c) which passes through the sieve (B), may be set as separate containers, and the sieve (A) may be installed in the container which gathers the fraction (1a) which does not pass through the sieve (A) and the sieve (B) may be installed in the container which gathers the fraction (1b) which passes through the sieve (A) and does not pass through the sieve (B). In such a case, it is possible to acquire the fraction (1b) by sieving the sample 1 and then acquiring a container in which the sieve (B) is installed.

(Step (II))

Step (II) is a step in which a colloidal solution having a density of 1.10 to 2.45 g/cm³ is added to the fraction (1b), centrifugation is performed, and the supernatant fraction (S0) after the centrifugation is acquired.

In step (II), the colloidal solution 2 having a density of 1.10 to 2.45 g/cm³ is added to the fraction (1b) (FIG. 6b). In the example of FIG. 6b, a fraction (1b) is placed in a centrifuge tube 21 and the colloidal solution 2 is added thereto to acquire the mixture 3 including the fraction (1b) and the colloidal solution 2. The colloidal solution 2 is not particularly limited as long as the colloidal solution 2 has a density of 1.10 to 2.45 g/cm³. The density of biological particles included in the fraction 1b is approximately 1.0 to 1.2 g/cm³ and the density of the sediment particles is approximately 2.5 to 2.8 g/cm³. Therefore, adding the colloidal solution 2 having a density of 1.10 to 2.45 g/cm³ to the fraction 1b makes it possible to separate the biological particles and sediment into a supernatant fraction and precipitate when centrifugation is performed. The density of the colloidal solution 2 is preferably 1.10 to 2.00 g/cm³, and more preferably 1.10 to 1.50 g/cm³.

In addition, the colloidal solution 2 preferably has a pH of 4.0 to 11.0. If the pH is within this range, it is possible to avoid adverse effects on the biological particles.

Examples of the colloidal solution 2 usable in step (II) include colloidal silica. In addition, as the colloidal solution 2, a commercially available solution may be used. For example, it is possible to use Ludox (registered trademark) HS-40 (Sigma Aldrich; density 1.3 g/cm³, pH 9.5-10.3), Percoll (registered trademark) (GE Healthcare; density 1.13 g/cm³, pH 9.0), RNAlater™ (Invitrogen; 1.25 g/cm³, pH 5.0), and the like, as the colloidal solution 2.

The amount of the colloidal solution 2 to be added is not particularly limited and may be any amount as long as it is possible to suspend the fraction (1b). For example, it is possible to set the addition amount of the colloidal solution 2 such that the sample 1:colloidal solution 2=1:1 to 5 as the volume ratio with the sample 1 before sieving.

After adding the colloidal solution 2 to the fraction (1b), the mixture 3 including the fraction (1b) and the colloidal solution 2 is subjected to centrifugation by a centrifuge 20 (FIG. 6c). Due to this, the mixture 3 is separated into a supernatant fraction (S0) and a precipitate (P0). The supernatant fraction (S0) includes an abundance of biological particles as a detection target, and the precipitate (P0) includes an abundance of sediment.

It is possible to appropriately select the conditions for centrifugation in this step depending on the type of biological particles as a detection target. For example, in a case where the detection target is meiofauna, examples of the conditions for centrifugation include 600 to 1000 G preferably 700 to 900 G, more preferably 750 to 850 G, and particularly preferably 800 G.

In addition, the time for centrifugation may be, for example, 3 to 30 minutes, preferably 5 to 20 minutes, more preferably 8 to 15 minutes, and particularly preferably 10 minutes.

After centrifugation, the supernatant fraction (S0) may be acquired using a pipette or the like.

It is possible to use the sample prepared by the method of pretreating a sample of the present embodiment, for example, as a sample for acquiring images of biological particles. For example, in an imaging apparatus provided with a flow cell as shown in FIG. 6d described below, it is possible to suitably use such a sample as a sample to be introduced in a flow cell.

According to the method of pretreating a sample of the present embodiment, even for samples containing a lot of sediment, it is possible to prepare a sample suitable for acquiring images of biological particles by efficiently removing the sediment. In addition, in a case where the sample prepared by the method of pretreating a sample of the present embodiment includes a colloidal solution, when the sample is introduced into a flow cell to acquire an image of the biological particles, it is possible to prevent settling of the biological particles in the flow cell and to prevent the flow cell from becoming clogged with biological particles.

In addition, the sample prepared by the method of pretreating a sample of the present embodiment can be used for various analyses such as genome analysis.

(Optional Steps)

The method of the present embodiment may further include a step of preparing a supernatant fraction (S0) in addition to step (I) and step (II) described above.

Examples of a step of preparing the supernatant fraction (S0) include a step of adding the colloidal solution 2 to the supernatant fraction (S0). The supernatant fraction (S0) usually includes the colloidal solution 2, but further adding the colloidal solution 2 makes it possible to adjust the buoyancy of the biological particles in the sample.

In addition, examples of a step of preparing the supernatant fraction (S0) also include a step in which a fraction which does not pass through the sieve (C) is acquired by sieving with a sieve (C) having meshes smaller than the meshes of the sieve (B) and, the colloidal solution 2 is added to the fraction. Sieving with a sieve (C) having meshes smaller than the meshes of the sieve (B) makes it possible to remove excess colloidal particles and concentrate the target biological particles. In addition, using a sieve having meshes smaller than the meshes of the sieve (B) makes it possible to reduce the loss of biological particles as a detection target. The meshes of the sieve (C) are not particularly limited as long as the meshes are smaller than the meshes of the sieve (B) used in step (I) and examples thereof include 30 to 63 µm.

The colloidal solution 2 to be used in this step may be the same as used in step (II).

Second Embodiment

In one embodiment, the present invention is a method of pretreating a sample for acquiring an image of biological particles, the method including a step of acquiring a fraction (1b) which passes through a sieve (A) having meshes of 250 to 1000 µm and does not pass through a sieve (B) having meshes of 32 to 63 µm by sieving a sample including biological particles as a detection target (hereinafter referred to as "step I"), a step in which a colloidal solution having a density of 1.10 to 2.45 g/cm³ is added to the fraction (1b), centrifugation is performed, and the supernatant fraction (S0) after the centrifugation is acquired (hereinafter referred to as "step II"), and a step of performing suspending a precipitate (Pn−1) after centrifugation in the colloidal solution to perform centrifugation, and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation) (hereinafter referred to as "step II'").

A description will be given of an outline of the method of the present embodiment with reference to FIGS. 1a to 1c, FIGS. 2a to 2c, and FIGS. 2a-n to c-n.

First, the sample 1 including biological particles as a detection target is sieved using a sieve (A) having meshes of 250 to 1000 µm and a sieve (B) having meshes of 32 to 63 µm to acquire a fraction (1b) which passes through the sieve (A) having meshes of 250 to 1000 µm and does not pass through the sieve (B) having meshes of 32 to 63 µm (FIG. 6a; step (I)).

Next, the colloidal solution 2 having a density of 1.10 to 2.45 g/cm³ is added to fraction (1b) and stirred appropriately (FIG. 6b). Thereafter, the mixture 3 including the fraction (1b) and the colloidal solution 2 is subjected to centrifugation to acquire a supernatant fraction (S0) (FIG. 6c) (the above is step (II)).

Figure 7:
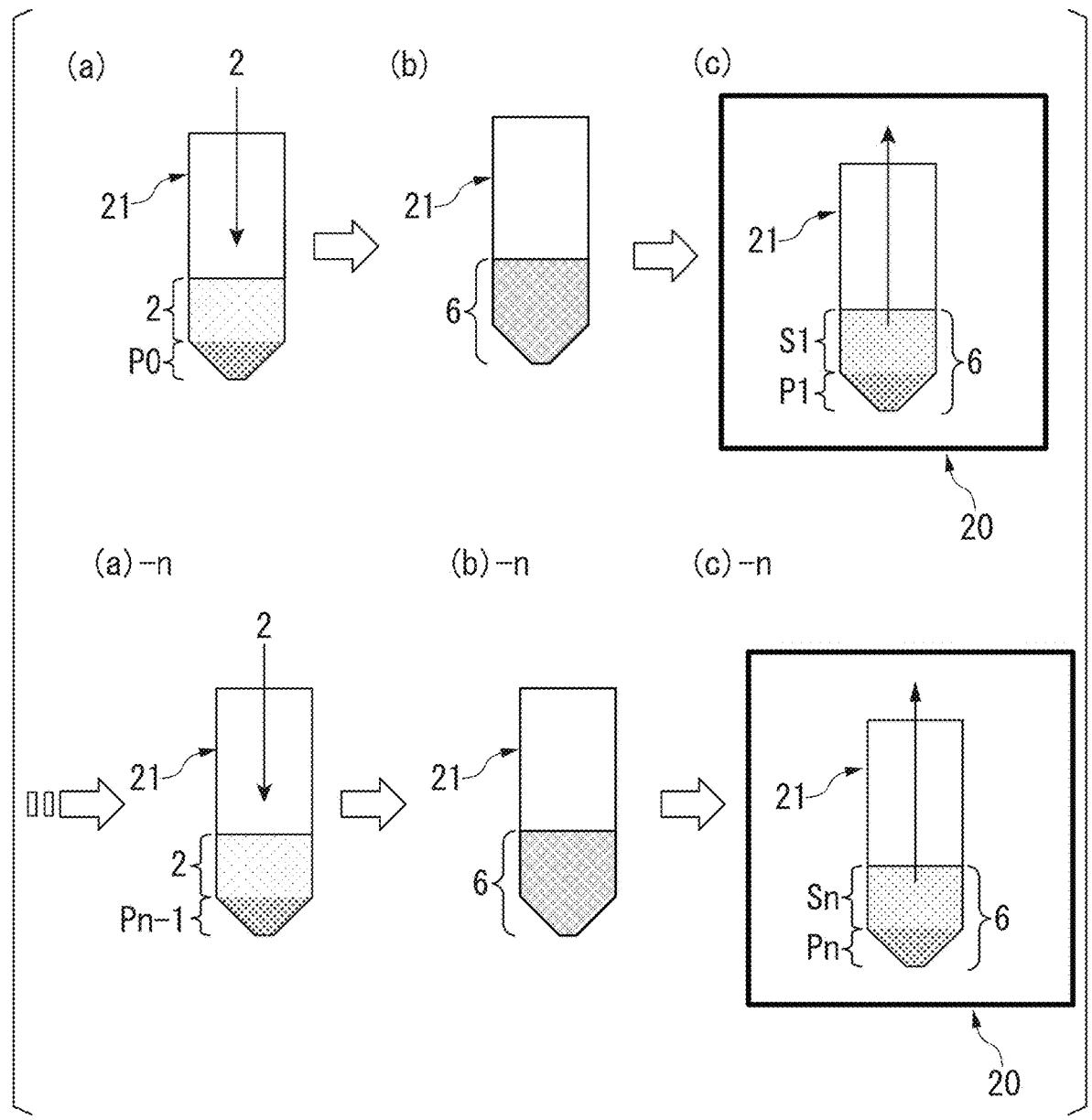
FIG. 7 shows an example of steps in the biological particle image acquiring method according to one embodiment of the present invention.

Next, the colloidal solution 2 is added to the precipitate (P0) after centrifugation (FIG. 7a), and the precipitate (P0) is suspended in the colloidal solution 2 to create a suspension 6 (FIG. 7b). Then, the suspension 6 is subjected to centrifugation to acquire a supernatant fraction (S1) (FIG. 7c). In this manner, the supernatant fractions (S1) to (Sn) after centrifugation n times are acquired (FIGS. 2a-n to c-n)) (the above is step (II')).

A description will be given below of each step of the method of the present embodiment.

(Step (I) and Step (II))

Step (I) and step (II) are the same as step (I) and step (II) in the method of the first embodiment described above. Therefore, explanation thereof is omitted.

(Step (II'))

Step (II') is a step of suspending a precipitate (Pn−1) after centrifugation in the colloidal solution to perform centrifugation and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation).

In step (II'), the colloidal solution 2 is added to the precipitate (P0) obtained by centrifugation in step (II) (FIG. 7a). The same colloidal solution 2 as used in step (II) may be used. Then, the precipitate (P0) is suspended in the colloidal solution 2 to obtain the suspension 6 (FIG. 7b). When the suspension 6 is subjected to centrifugation, the suspension 6 is separated into a supernatant fraction (S1) and a precipitate (P1) (FIG. 2c). Biological particles remaining in the precipitate (P0) transfer to the supernatant fraction (S1) while sediment remains in the precipitate (P1).

The centrifugation conditions described above may be the same as or different from those of the centrifugation in step (II), but are preferably the same. After centrifugation, a supernatant fraction (S1) may be acquired using a pipette or the like.

The colloidal solution 2 is again added to the precipitate (P1) obtained by the centrifugation described above, as necessary, and is suspended and subjected to centrifugation. Then, a supernatant fraction (S2) obtained after centrifugation is acquired. When the supernatant fraction obtained by the n$^{th}$ centrifugation in this manner is the supernatant fraction (Sn) and the precipitate obtained by the n$^{th}$ centrifugation is the precipitate (Pn), it is possible to acquire the supernatant fractions (S1) to (Sn) by adding the colloidal solution 2 to the precipitate (Pn−1), carrying out suspension, and performing centrifugation n times.

In this step, n may be an integer of 1 or more, and the number of times of centrifugation is not particularly limited. As the number of times of centrifugation is increased (as n is increased), it is possible to increase the recovery rate of biological particles remaining in the precipitate (Pn). Normally, it is possible for n to be an integer of 1 to 5, and n may be an integer of 1 to 3, for example, n can be 2 or 3.

The added amount of the colloidal solution 2 to the precipitate (Pn−1) is not particularly limited as long as it is an amount in which it is possible to suspend the precipitate (Pn-1). Depending on the amount of precipitate (Pn-1), an appropriate amount of colloidal solution 2 may be added thereto to suspend the precipitate (Pn-1). Examples of the amount of the colloidal solution 2 to be added include precipitate (Pn-1): colloidal solution 2=2:3, or the like as the volume ratio with the precipitate (Pn-1).

The sample pretreated by the method of the present embodiment usually includes the colloidal solution 2. The supernatant fraction (S0) obtained in step (II) and the supernatant fractions (S1) to (Sn) obtained in step (II') are mixed partially or wholly and it is possible to use the result for image acquisition, analysis, or the like as described below.

It is possible to use the sample prepared by the method of pretreating a sample of the present embodiment as a sample for acquiring an image of biological particles in the same manner as the sample prepared by the method of the first embodiment.

According to the method of the present embodiment, it is possible to efficiently remove sediment to prepare a sample suitable for acquiring images of biological particles, even for samples containing a lot of sediment. In addition, in step (II'), since the colloidal solution is added to the precipitate obtained by centrifugation and further centrifugation is carried out, it is possible to recover the biological particles even in a case where the biological particles remain in the precipitate.

In addition, it is possible to subject the sample prepared by the method of pretreating a sample of the present embodiment to various analyses such as genome analysis in the same manner as the sample prepared by the method of the first embodiment.

(Optional Steps)

In the method of the present embodiment, a step of preparing the supernatant fraction (S0) and the supernatant fractions (S1) to (Sn) may be included in addition to the above steps (T), (1I), and (IF).

Examples of a step of preparing the supernatant fraction (S0) and supernatant fractions (S1) to (Sn) include a step of adding the colloidal solution 2 to the supernatant fraction (S0) and supernatant fractions (S1) to (Sn). Usually, the supernatant fraction (S0) and the supernatant fractions (S1) to (Sn) include the colloidal solution 2, but further adding the colloidal solution 2 makes it possible to adjust the buoyancy of the biological particles in the sample.

The colloidal solution 2 may be added individually to each of the supernatant fraction (S0) and the supernatant fractions (S1) to (Sn), and may be added to a part or the whole of a mixture of the supernatant fraction (S0) and the supernatant fractions (S1) to (Sn). In a case where the colloidal solution 2 is individually added to each of the supernatant fraction (S0) and the supernatant fractions (S1) to (Sn), the supernatant fraction (S0) and supernatant fractions (S1) to (Sn) may be mixed in part or in whole after the addition of the colloidal solution 2.

In addition, examples of a step of preparing the supernatant fraction (S0) and the supernatant fractions (S1) to (Sn) also include a step of acquiring a fraction which does not pass through the sieve (C) by sieving with the sieve (C) having meshes smaller than the meshes of the sieve (B) and adding the colloidal solution 2 to the fraction. Sieving with a sieve (C) having meshes smaller than the meshes of the sieve (B) makes it possible to remove excess colloidal particles to concentrate the biological particles which are the target. In addition, using a sieve having meshes smaller than the meshes of the sieve (B) makes it possible to reduce the loss of the biological particles as a detection target. The meshes of the sieve (C) are not particularly limited as long as the meshes are smaller than the meshes of the sieve (B) used in step (I) and examples thereof include 30 to 63 µm.

The colloidal solution 2 to be used in this step may be the same as used in step (II).

The sieving using the sieve (C) may be performed individually for each of the supernatant fraction (S0) and the supernatant fractions (S1) to (Sn), or may be performed for a part or the whole of a mixture of the supernatant fraction (S0) and the supernatant fractions (S1) to (Sn). In a case where the sieving and the addition of the colloidal solution 2 are performed individually for each of the supernatant fraction (S0) and the supernatant fractions (S1) to (Sn), after the sieving and addition of the colloidal solution 2, a part or the whole of the obtained sample may be mixed.

Method of Acquiring Image of Biological Particles

First Embodiment

In one embodiment, the present invention is a method of acquiring an image of biological particles including a step of acquiring a fraction (1b) which passes through a sieve (A) having meshes of 250 to 1000 µm and does not pass through a sieve (B) having meshes of 32 to 63 µm by sieving a sample including biological particles as a detection target (hereinafter referred to as "step I"), a step in which a colloidal solution having a density of 1.10 to 2.45 g/cm; is added to the fraction (1b), centrifugation is performed, and the supernatant fraction (S0) after the centrifugation is acquired (hereinafter referred to as "step II"), and a step of allowing a fluid including at least a part of the supernatant fraction (S0) to flow in a flow cell and imaging the fluid flowing in the flow cell (hereinafter referred to as "step III").

A description will be given of the outline of the method of the present embodiment with reference to FIGS. 1a to 1e.

First, the sample 1 including biological particles as a detection target is sieved using a sieve (A) having meshes of 250 to 1000 µm and a sieve (B) having meshes of 32 to 63 µm, and a fraction (I b) which passes through the sieve (A) having meshes of 250 to 1000 µm and does not pass through the sieve (B) having meshes of 32 to 63 µm is acquired (FIG. 6a; step (I)).

Next, the colloidal solution 2 having a density of 1.10 to 2.45 g/cm³ is added to the fraction (1b) and stirred appropriately (FIG. 6b). Thereafter, the mixture 3 including the fraction (1b) and the colloidal solution 2 is subjected to centrifugation to acquire a supernatant fraction (S0) (FIG. 6c) (the above is step (II)).

Next, while allowing a fluid 4 including at least a part of the supernatant fraction (S0) to flow in a flow cell 31, the flow cell 31 in a frame 40 is imaged by a camera 32 (FIG. 6d; step (III)). In the example of FIG. 6d, imaging is performed via an objective lens 33.

Due to this, at the time of imaging, it is possible to acquire an image 41 of the biological particles 5b present in the frame 40.

A description will be given of each step of the method of the present embodiment below.

(Step (I) and Step (II))

Step (I) and step (II) are the same as step (I) and step (II) in the "<Method of Pretreating Sample Including Biological Particles>" described above. Therefore, explanation thereof is omitted.

(Step (III))

Step (III) is a step of allowing a fluid including at least a part of the supernatant fraction (S0) to flow in the flow cell and imaging the fluid flowing in the flow cell.

In step (III), first, the fluid 4 including at least a part of the supernatant fraction (S0) is allowed to flow in the flow cell 31. The fluid 4 flowing in the flow cell 31 preferably includes the colloidal solution 2. Including the colloidal solution 2 in the fluid 4 makes it possible to prevent precipitation of the biological particles as the detection target and to prevent the clogging of the flow cell 31 with the biological particles.

Since the supernatant fraction (S0) usually includes the colloidal solution 2, the supernatant fraction (S0) may be allowed to flow as the fluid 4 in the flow cell 31 as it is. In addition, a supernatant fraction (S0) to which the colloidal solution 2 is further added may be allowed to flow as the fluid 4 in the flow cell 31.

In addition, the supernatant fraction (S0) may be subjected to a treatment such as sieving to acquire a predetermined fraction, and thereby the fluid 4 may be prepared to be allowed to flow in the flow cell 31. For example, the fluid 4 may be obtained by removing excess colloidal particles from the supernatant fraction (S0) using a sieve (C) having meshes smaller than the meshes of the sieve (B), acquiring a fraction which does not pass through the sieve (C), and adding the colloidal solution 2 to the fraction. That is, the fluid 4 may include a fluid obtained by sieving the supernatant fraction (S0) with a sieve (C) having meshes smaller than the meshes of the sieve (B) to acquire a fraction which does not pass through the sieve (C), and adding the colloidal solution 2 to the fraction. Sieving with a sieve (C) having meshes smaller than the meshes of the sieve (B) makes it possible to remove excess colloidal particles to concentrate the biological particles as a target and to perform the imaging efficiently. In addition, using a sieve having meshes smaller than the meshes of the sieve (B) makes it possible to reduce the loss of the biological particles as a detection target. The meshes of the sieve (C) are not particularly limited as long as the meshes are smaller than the meshes of the sieve (B) used in step (I) and examples thereof include 30 to 63 μm.

In this step, while allowing the fluid 4 including at least a part of the supernatant fraction (S0) prepared as described above to flow in the flow cell 31, the fluid 4 flowing in the flow cell 31 is imaged. In the example of FIG. 6d, the fluid 4 flowing in the flow cell 31 is imaged by the camera 32 installed in an imaging apparatus 30 via the objective lens 33. In the example of FIG. 6d, the imaging portion (frame 40) of the flow cell 31 is irradiated with light by a light source 34.

The flow cell 31 preferably has high transparency to enable imaging of the fluid 4 flowing inside. Although the shape of the flow cell 31 is not particularly limited, the shape of the flow cell 31 is preferably a shape where the surface imaged by the camera 32 is a flat surface. Examples of the shape of the flow cell 31 include a rectangular parallelepiped. The size of the flow cell 31 is not particularly limited and is able to be appropriately selected according to the biological particles as the detection target. For example, in a case where the detection target is meiofauna, it is possible to use the flow cell 31 having an inner diameter of 150 to 500 μm in the depth direction with respect to the imaging plane of the camera 32. The inner diameter is preferably 200 to 400 μm, and more preferably 250 to 350 μm.

Herein, the term "inner diameter in the depth direction" of the flow cell means the inner diameter of the flow cell in the direction orthogonal to the imaging plane. In addition, the term "inner diameter in the width direction" of the flow cell means the inner diameter of the flow cell in a direction parallel to the imaging surface.

The method of introducing the fluid 4 into the flow cell 31 is not particularly limited. For example, the introduction may be carried out using pipetting or the like, or may be performed by connecting a tube to the upstream side of the flow cell 31 and bringing the upstream end of the tube into contact with the fluid 4 in a container or the like to suction up the fluid 4. In addition, it is possible to create the flow of the fluid 4 in the flow cell 31, for example, by connecting a pump to the downstream side of the flow cell 31 via a tube or the like and operating the pump, or the like. In addition, the inside of the flow cell 31 (in a case where a tube is connected to the upstream side of the flow cell 31, the inside of the tube as well) is preferably filled with the colloidal solution 2 before introducing the fluid 4 into the flow cell 31.

In the example of FIG. 6d, imaging is performed by the camera 32 via the objective lens 33. Using the objective lens 33 makes it possible to acquire an enlarged image of the biological particles. The magnification of the objective lens 33 is not particularly limited and is able to be appropriately selected according to the biological particles as the detection target. For example, in a case where the detection target is meiofauna, it is possible to use an objective lens with a magnification of 1 to 20 times, and the magnification is preferably 2 to 10 times, and the magnification is more preferably 2 to 5 times. Imaging may be performed without using the objective lens 33 and the image enlargement processing may be performed after imaging.

In addition, in the example of FIG. 6d, the light source 34 irradiates the imaging portion with light to perform imaging. Performing the imaging by irradiating the imaging portion with light makes it possible to acquire a clearer image. The light source 34 may intermittently irradiate light in accordance with the imaging or may constantly irradiate light. The light to be irradiated is not particularly limited, but is preferably visible light. In step (I), in a case where a sample dyed with a fluorescent dye is used as the sample 1, the sample may be irradiated with light having a wavelength which excites the fluorescent dye.

In addition, in the example of FIG. 6d, the camera 32 acquires the image of the fluid 4 present in the frame 40 on the flow cell 31. The image imaged by the camera 32 may be a still image or may be a moving image. In a case of imaging a still image, the camera 32 preferably performs imaging at predetermined time intervals. The imaging interval may be appropriately selected according to the flow velocity of the fluid 4 flowing in the flow cell 31. It is possible for the imaging interval to be, for example, 5 to 50 times/second or the like.

In the imaging apparatus 30 having the above-described configuration, when the fluid 4 including at least a part of the supernatant fraction (S0) is allowed to flow in the flow cell 31, biological particles 5a to 5c included in the fluid 4 move in the flow cell 31 according to the flow of the fluid 4. Meanwhile, the camera 32 continuously acquires the images of the frame 40 on the flow cell 31. Therefore, when the biological particles 5a to 5c move into the frame 40, images of the biological particles 5a to 5c are imaged. In the example of FIG. 6d, images of the biological particles 5b are imaged. As a result, it is possible to acquire the image 41 of the biological particles 5b (FIG. 6e).

It is possible to use images of biological particles acquired by the method of the present embodiment for analysis for classifying organism species. For example, classifying images acquired by the method of the present embodiment by visual observation or an image analysis program or the like makes it possible to analyze biota quickly as compared with the methods using microscopes in the related art.

According to the method of the present embodiment, since it is possible to remove sediment by a sieving treatment and a centrifugation treatment, it is possible to efficiently acquire images of biological particles even for samples including sediment. In addition, in a case where the fluid flowing in a flow cell includes a colloidal solution, it is possible to prevent precipitation of the biological particles in the flow cell and to prevent the clogging of the flow cell with biological particles.

(Optional Step)

In addition to the above steps (I) to (III), the method of the present embodiment may further include a step of recovering the fluid 4 for which the imaging is finished. Recovering the fluid 4 for which the imaging is finished makes it possible to carry out further analysis of the biological particles included in the fluid 4.

In a case of recovering the fluid 4 which the imaging is finished, for example, a tube or the like may be connected to the downstream side of the flow cell 31 and the downstream end of the tube may be installed in a sealed container or the like. If a pump or the like is connected to the sealed container so as to discharge the air in the sealed container, it is possible to create a flow of the fluid 4 in the flow cell 31, and furthermore, it is possible to recover the fluid 4 for which the imaging is finished in the sealed container.

The biological particles included in the fluid 4 recovered as described above are not crushed by a pump or the like and are hardly damaged. Therefore, it is possible to use the biological particles for further analysis.

Second Embodiment

In one embodiment, the present invention is a method of acquiring an image of biological particles including a step of acquiring a fraction (1b) which passes through a sieve (A) having meshes of 250 to 1000 μm and does not pass through a sieve (B) having meshes of 32 to 63 μm by sieving a sample including biological particles as a detection target (hereinafter referred to as "step I"), a step in which a colloidal solution having a density of 1.10 to 2.45 g/cm$^3$ is added to the fraction (1b), centrifugation is performed, and the supernatant fraction (S0) after the centrifugation is acquired (hereinafter referred to as "step II"), and a step of performing suspending a precipitate (Pn-1) after centrifugation in the colloidal solution to perform centrifugation, and acquiring a supernatant fraction (Sn) after the centrifugation, n times (n is an integer of 1 or more, the precipitate (Pn-1) is a precipitate obtained after the (n-1)$^{th}$ centrifugation, and the supernatant fraction (Sn) is the supernatant fraction obtained after the n$^{th}$ centrifugation) (referred to below as "step II'"), a step of allowing a fluid including at least a part of the supernatant fraction (S0) and the supernatant fractions (S1) to (Sn) of the n times to flow in the flow cell and imaging the fluid flowing in the flow cell (hereinafter referred to as "step III'").

A description will be given of the outline of the method of the present embodiment with reference to FIGS. 1a to 1e, FIGS. 2a to c, and FIGS. 2a-n to c-n.

First, the sample 1 including biological particles as a detection target is sieved using a sieve (A) having meshes of 250 to 1000 μm and a sieve (B) having meshes of 32 to 63 μm, and a fraction (1b) which passes through the sieve (A) having meshes of 250 to 1000 μm and does not pass through the sieve (B) having meshes of 32 to 63 μm is acquired (FIG. 6a; step (I)).

Next, the colloidal solution 2 having a density of 1.10 to 2.45 g/cm$^3$ is added to the fraction (1b) and stirred appropriately (FIG. 6b). Thereafter, the mixture 3 including the fraction (1b) and the colloidal solution 2 is subjected to centrifugation to acquire a supernatant fraction (S0) (FIG. 6c) (the above is step (II)).

Next, the colloidal solution 2 is added to the precipitate (P0) after centrifugation (FIG. 7a), and the precipitate (P0) is suspended in the colloidal solution 2 to create the suspension 6 (FIG. 7b). Then, the suspension 6 is subjected to centrifugation to acquire a supernatant fraction (S1) (FIG. 7c). In this manner, the supernatant fractions (S1) to (Sn) after n times of centrifugation are acquired (FIGS. 2a-n to c-n)) (the above is step (II')).

Next, while allowing the fluid 4 including at least a part of the supernatant fraction (S0) and the supernatant fractions (S1) to (Sn) of the n times to flow in the flow cell 31, the flow cell 31 in the frame 40 is imaged by the camera 32 (FIG. 6d; step (III')). In the example of FIG. 6d, imaging is performed via the objective lens 33. Due to this, at the time of imaging, it is possible to acquire the image 41 of the biological particles 5b present in the frame 40. A description will be given below of each step of the method of the present embodiment.

(Step (I), Step (II), and Step (II'))

Step (I), step (II) and step (II') are the same as step (I), step (II) and step (II') in the above "<Method of Pretreating Sample Including Biological Particles>". Therefore, explanation thereof will be omitted.

(Step (III'))

Step (III') is a step of allowing a fluid including at least a part of the supernatant fraction (S0) and the supernatant fractions (S1) to (Sn) of the n times to flow in a flow cell and imaging the fluid flowing in the flow cell.

In step (III'), the fluid 4 including at least a part of supernatant fractions (S0) obtained in step (II) and supernatant fractions (S1) to (Sn) obtained in step (II') is allowed to flow in the flow cell 31. A part or all of the supernatant fraction (S0) and the supernatant fraction (S1) to (Sn) may be mixed, and the fluid 4 may be prepared so as to include at least a part of the mixture. Preferably, all of the supernatant fraction (S0) and the supernatant fractions (S1) to (S0) are mixed and the fluid 4 is prepared to include at least a part of the mixture.

In the same manner as the method of the first embodiment, the fluid 4 flowing in the flow cell 31 preferably includes the colloidal solution 2. Since the supernatant fraction (S0) and the supernatant fractions (S1) to (Sn) usually include the colloidal solution 2, the supernatant fraction (S0) and the supernatant fractions (S1) to (Sn) may be allowed to flow into the flow cell 31 as the fluid 4 as it is. In addition, the supernatant fraction (S0) and the supernatant fractions (S1) to (Sn) to which the colloidal solution 2 is further added may be allowed to flow as the fluid 4 in the flow cell 31. In a case where a mixture of the supernatant fraction (S0) and the supernatant fractions (S1) to (Sn) is used, the colloidal solution 2 may be added to the mixture.

In addition, in the same manner as the method of the first embodiment, the fluid 4 may be prepared by further subjecting the supernatant fraction (S0) and the supernatant fractions (S1) to (Sn) to treatments such as sieving to acquire a predetermined fraction, and allowed to flow in the flow cell 31. For example, the fluid 4 may be obtained by sieving the supernatant fraction (S0) and the supernatant fractions (S1)

to (Sn) using a sieve (C) having meshes smaller than meshes of the sieve (B), acquiring a fraction which does not pass through the sieve (C), and adding the colloidal solution 2 to the fraction. The sieving using the sieve (C) and the addition of the colloidal solution 2 may be performed individually for each of the supernatant fraction (S0) and the supernatant fractions (S1) to (Sn) respectively or may be performed on a mixture of part or all of the fraction (S0) and supernatant fractions (S1) to (Sn). In a case where the sieving and the addition of the colloidal solution 2 are performed individually for each of the supernatant fraction (S0) and the supernatant fractions (S1) to (Sn), a part or the whole of the obtained sample may be mixed after sieving and addition of the colloidal solution 2. That is, the fluid 4 may include a fluid in which the supernatant fraction (S0) and/or the supernatant fractions (S1) to (Sn) are sieved with a sieve (C) having meshes smaller than the meshes of the sieve (B) to acquire a fraction which does not pass through the sieve (C) and the colloidal solution 2 is added thereto. In addition, in a case where a mixture of the supernatant fraction (S0) and the supernatant fractions (S1) to (Sn) is used, the fluid 4 may be a fluid obtained by using the sieve (C) to sieve the mixture to acquire a fraction which does not pass through the sieve (C), and adding the colloidal solution 2 to the fraction. Sieving with a sieve (C) having meshes smaller than the meshes of the sieve (B) makes it possible to remove excess colloidal particles to concentrate the biological particles as a target and to perform the imaging efficiently. In addition, using a sieve having meshes smaller than the meshes of the sieve (B) makes it possible to reduce the loss of biological particles as a detection target. The meshes of the sieve (C) are not particularly limited as long as the meshes are smaller than the meshes of the sieve (B) used in step (I) and examples thereof include 30 to 63 μm.

In this step, while allowing the fluid 4 including at least a part of the supernatant fraction (S0) and the supernatant fractions (S1) to (Sn) prepared as described above to flow in the flow cell 31, the fluid 4 flowing in the flow cell 31 is imaged. It is possible for the flow cell 31 to be the same as in the method of the first embodiment. In addition, it is also possible for the method of introducing the fluid 4 into the flow cell 31, the method of imaging the fluid 4 flowing in the flow cell 31, and the like, to be performed with the same methods as the methods of the first embodiment.

It is possible to use images of biological particles acquired by the method of the present embodiment for analysis for classifying organism species in the same manner as the image acquired by the method of the first embodiment.

According to the method of the present embodiment, since it is possible to remove sediment by a sieving treatment and a centrifugation treatment, it is possible to efficiently acquire images of biological particles even for samples including sediment. In addition, in step (II'), since the colloidal solution is added to the precipitate obtained by centrifugation and further centrifugation is carried out, it is possible to recover the biological particles even in a case where the biological particles remain in the precipitate.

(Optional Step)

In the same manner as the method of the first embodiment, the method of the present embodiment may further include a step of recovering the fluid 4 for which the imaging is finished in addition to steps (I), (II), (II'), and (III') described above. Recovering the fluid 4 for which the imaging is finished makes further analysis of the biological particles included in the fluid 4 possible. The method of recovering the fluid 4 for which the imaging is finished may also be performed in the same manner as in the method of the first embodiment.

<Apparatus for Pretreating Sample Including Biological Particles>

In one embodiment, the present invention provides an apparatus for pretreating a sample including biological particles for realizing the method of pretreating a sample including biological particles described above. An apparatus for pretreating a sample including biological particles according to the present embodiment is provided with a sieving section which is provided with a sieve (A) having meshes of 250 to 1000 μm and a sieve (B) having meshes of 32 to 63 μm, and which performs sieving of a sample including biological particles as a detection target to acquire a fraction (1b) which passes through the sieve (A) and does not pass through the sieve (B); a colloidal solution addition section for adding a colloidal solution to the fraction (1b) acquired by the sieving section; a centrifugation section for subjecting the fraction (1b) to which the colloidal solution was added to centrifugation; and a supernatant fraction-acquiring section for acquiring a supernatant fraction after the centrifugation in the centrifugation section.

A description will be given below of an example of a configuration of an apparatus for pretreating a sample including biological particles according to the present embodiment.

Figure 8:
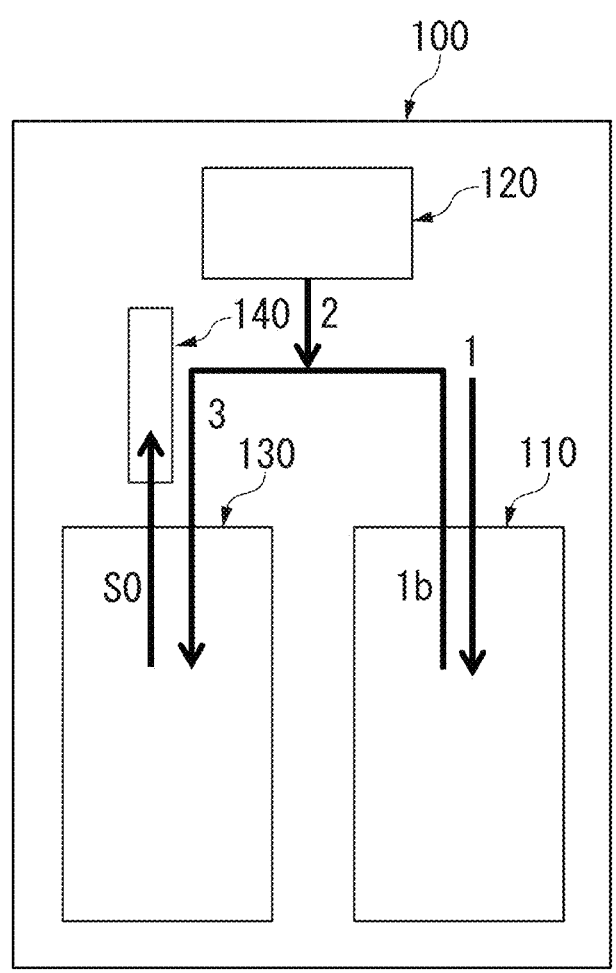
FIG. 8 shows a configuration example of a pretreatment apparatus for a sample including biological particles according to one embodiment of the present invention.

FIG. 8 shows an example of a configuration of an apparatus for pretreating a sample including biological particles of the present embodiment. A pretreatment apparatus 100 shown in FIG. 8 is provided with a sieving section 110, a colloidal solution addition section 120, a centrifugation section 130, and a supernatant fraction-acquiring section 140.

The sieving section 110 is a unit for sieving the sample 1 including biological particles as a detection target and acquiring a fraction (1b) which passes through a sieve (A) having meshes of 250 to 1000 μm and does not pass through a sieve (B) having meshes of 32 to 63 μm. The sieving section 110 is provided with at least a sieve (A) having meshes of 250 to 1000 μm and a sieve (B) having meshes of 32 to 63 μm, and the sample 1 is sieved by these sieves. The sieving section 110 may be configured as shown in FIG. 6a, for example. In the example of FIG. 6a, there is a configuration in which a sieve (A) having meshes of 250 to 1000 μm and a sieve (B) having meshes of 32 to 63 μm are installed in the container 10, and sieving is performed while carrying out shaking with the shaker 13. After finishing the sieving, a fraction (1b) which passes through the sieve (A) having meshes of 250 to 1000 μm and does not pass through the sieve (B) having meshes of 32 to 63 μm is acquired.

Here, the configuration of the sieving section 110 is not limited to the example in FIG. 6a, and for example, the sieve (A) and the sieve (B) may be installed in separate containers. In such a case, after finishing the sieving, it is possible to separate the containers in which each sieve is installed and to acquire fractions (1b) for each container in which the sieve (B) is installed.

The colloidal solution addition section 120 is a unit for adding the colloidal solution 2 to the fraction (1b) acquired by the sieving section 110. The colloidal solution 2 is the same as used in step (II) in "<Method of Acquiring Image of Biological Particles>" described above. It is possible to configure the colloidal solution addition section 120, for example, to add the colloidal solution 2 to the fraction (I b) with a pipette, a tube, a glass tube, or the like.

The centrifugation section 130 is a unit for performing centrifugation on the fraction (1b) to which the colloidal solution 2 was added in the colloidal solution addition section 120. In FIG. 8, a mixture of the fraction (1b) and the colloidal solution 2 is shown as the mixture 3. It is possible for the centrifugation section 130 to be provided with a typical centrifuge. The conditions for centrifugation in the centrifugation section 130 may be set by an operation panel or the like.

The supernatant fraction-acquiring section 140 is a unit for acquiring a supernatant fraction (S0) after the centrifugation in the centrifugation section 130. The supernatant fraction-acquiring section 140 may acquire the supernatant fraction (S0) with, for example, a pipette, a tube, a glass tube, or the like, or may be configured to move the supernatant fraction (S0) directly from a centrifuge tube to another container.

A description will be given of an example of the operation of the pretreatment apparatus 100 provided with the above configuration.

First, the sample 1 including biological particles as a detection target is put into the sieving section 110. In the sieving section 110, the sample 1 is sieved, and a fraction (1b) which passes through a sieve having meshes of 250 to 1000 μm and does not pass through a sieve having meshes of 32 to 63 μm is acquired. Many of the sediment particles included in the sample 1 are removed by sieving with the sieving section 110.

The colloidal solution 2 is added by the colloidal solution addition section 120 to the fraction (1b) acquired by the sieving section 110. Due to this, the mixture 3 of the fraction (1b) and the colloidal solution 2 is prepared.

The mixture 3 is introduced into the centrifugation section 130 and subjected to centrifugation. Due to this, the mixture 3 is separated into a supernatant fraction (S0) and a precipitate (P0). The supernatant fraction (S0) includes the biological particles as a detection target and the precipitate (P0) includes sediment particles. It is possible to acquire a supernatant fraction (S0) including almost no sediment particles by centrifugation in the centrifugation section 130. Thereafter, the supernatant fraction (S0) is acquired by the supernatant fraction-acquiring section 140 and is appropriately prepared to complete the pretreatment of the sample including the biological particles.

Since the pretreatment apparatus for a sample including biological particles of the present embodiment is provided with the above-described configuration, it is possible to prepare a sample having sufficient quality for subsequent analysis even for a sample including a lot of sediment particles. In addition, the sample prepared by the pretreatment apparatus for a sample including biological particles according to the present embodiment makes it possible to acquire an image having sufficient image quality for subsequent analysis in a case where an image of biological particles is acquired by an image-acquiring apparatus or the like.

Here, the pretreatment apparatus 100 may be provided with other configurations than the configurations described above. For example, the pretreatment apparatus 100 may be provided with a precipitation suspension section. The precipitation suspension section is a unit for suspending the precipitate after the centrifugation in the centrifugation section 130 and adding the colloidal solution 2 to the precipitate (P0) after the supernatant fraction (S0) is acquired by the supernatant fraction-acquiring section 140. The precipitate (P0) suspended in the colloidal solution 2 in the precipitation suspension section is again subjected to centrifugation in the centrifugation section 130. After centrifugation, the supernatant fraction (S1) is acquired by the supernatant fraction-acquiring section 140. Due to this, it is possible to recover the biological particles even in a case where biological particles as a detection target remain in the precipitate (P0). In addition, the precipitate (P1) obtained by centrifugation again may be further suspended in the colloidal solution 2 in the precipitation suspension section, and centrifugation may be performed again in the centrifugation section 130. In this manner, when the supernatant fraction obtained by the $n^{th}$ centrifugation is the supernatant fraction (Sn) and the precipitate obtained by the $n^{th}$ centrifugation is precipitate (Pn), the colloidal solution 2 may be added to the precipitate (Pn−1) to cause suspension, and subjected to centrifugation n times. The number of times to suspend the precipitates (P0) to (Pn−1) in the precipitation suspension section may be set by an operation panel or the like.

The precipitation suspension section may be configured to suspend the precipitate by adding the colloidal solution 2 to a centrifuge tube with a pipette, a tube, a glass tube, or the like after acquiring the supernatant fraction and shaking the centrifuge tube, or may be configured to suspend the precipitate by performing pipetting or the like after the addition of the colloidal solution 2. In addition, it is also possible for the colloidal solution addition section 120 to perform the addition of the colloidal solution 2.

In addition, the pretreatment apparatus 100 may be provided with a supernatant fraction preparation section. The supernatant fraction preparation section is a unit for further preparing the supernatant fractions (S0) to (Sn) acquired by the supernatant fraction-acquiring section 140 for subsequent analysis. For example, it is possible for the supernatant fraction preparation section to be configured to mix the supernatant fractions (S0) to (Sn) acquired by the supernatant fraction-acquiring section 140. In addition, a configuration may be provided in which a colloidal solution is added to the supernatant fractions (S0) to (Sn). Alternatively, a configuration may be provided in which a sieve (C) having meshes smaller than the meshes of the sieve (B) is provided, a fraction which does not pass through the sieve (C) is acquired by sieving the supernatant fractions (S0) to (Sn), and a colloidal solution is added to the fraction.

It is possible for the pretreatment apparatus 100 to be further provided with a control section or the like for controlling the operation of the entire apparatus.

<Biological Particle Image-Acquiring Apparatus>

In one embodiment, the present invention provides a biological particle image-acquiring apparatus for realizing the method of acquiring an image of biological particles described above. The biological particle image-acquiring apparatus of the present embodiment is provided with a sieving section which is provided with a sieve (A) and a sieve (B) having meshes smaller than meshes of the sieve (A), and which performs sieving of a sample including biological particles as a detection target to acquire a fraction (1b) which passes through the sieve (A) and does not pass through the sieve (B); a colloidal solution addition section for adding a colloidal solution to the fraction (1b) acquired by the sieving section; a centrifugation section for subjecting the fraction (1b) to which the colloidal solution was added to centrifugation; a supernatant fraction-acquiring section for acquiring a supernatant fraction after the centrifugation in the centrifugation section; and an imaging section which is provided with a flow cell and a camera and which allows a fluid including at least a part of the supernatant fraction acquired by the supernatant fraction-acquiring section to flow in the flow cell and images the fluid flowing in the flow cell with the camera. The sieve (A) has meshes smaller than whichever is larger of either of an inner diameter of the flow cell in a width direction and a depth direction.

A description will be given below of an example of the configuration of the biological particle image-acquiring apparatus of the present embodiment.

Figure 9:
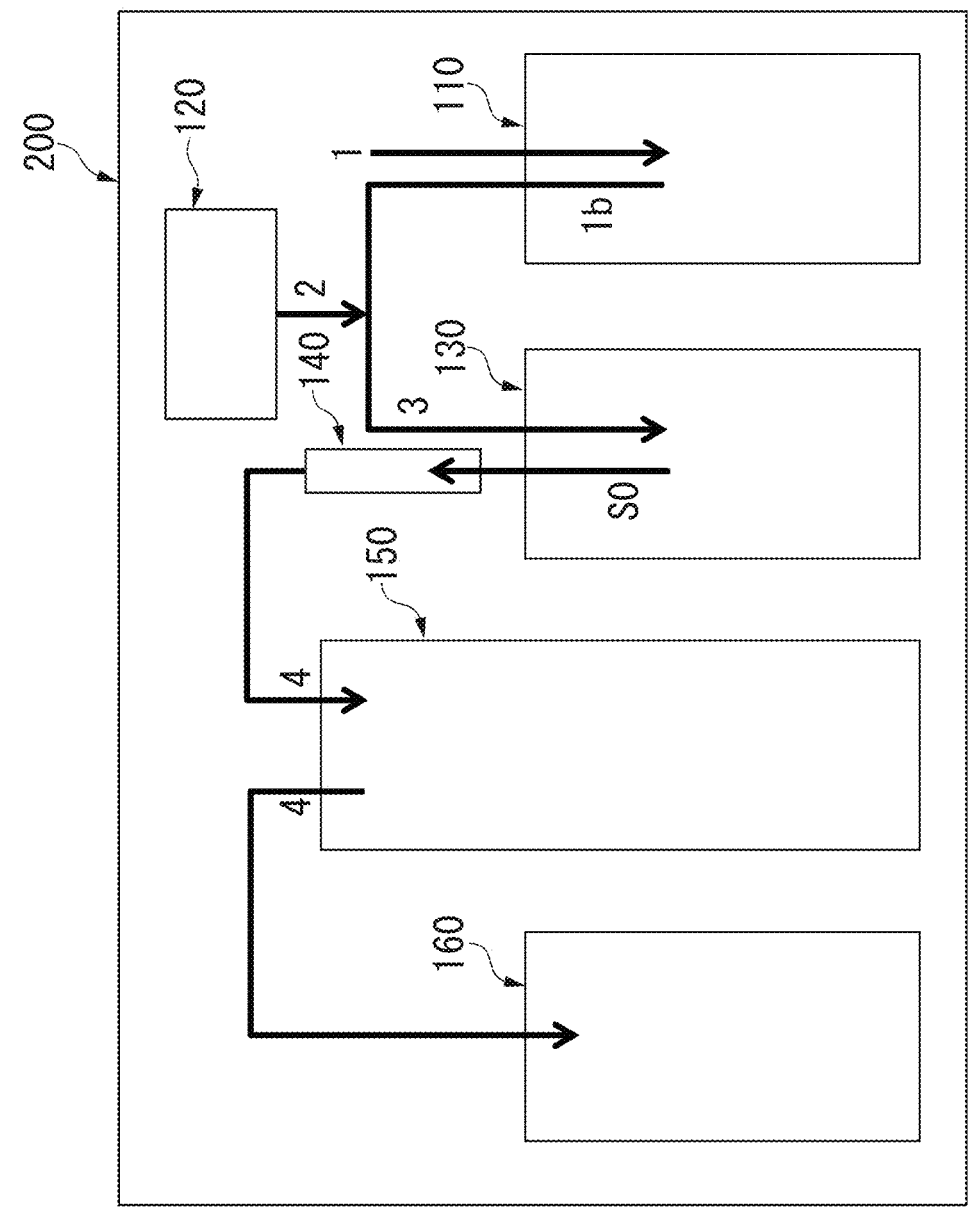
FIG. 9 shows a configuration example of a biological particle image acquiring apparatus according to one embodiment of the present invention.
Figure 10:
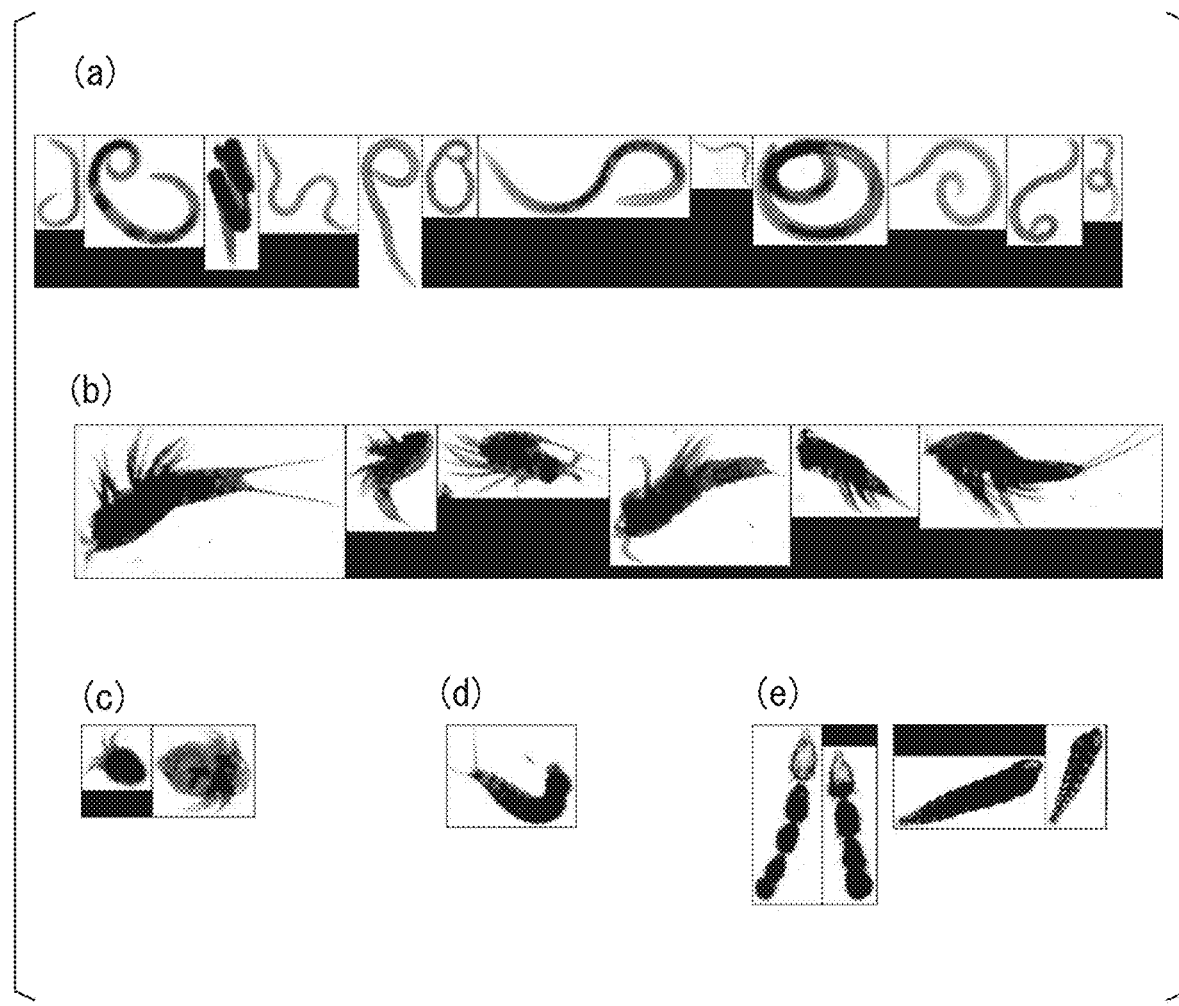
FIG. 10 shows examples of images of meiofauna acquired by a method according to one embodiment of the present invention. (a) shows nematodes, (b) shows copepods, (c) shows nauplius larvae, (d) shows kinorhyncha, and (e) shows foraminifers.

FIG. 9 shows an example of the configuration of the biological particle image-acquiring apparatus of the present embodiment. The biological particle image-acquiring apparatus 200 shown in FIG. 9 is provided with the sieving section 110, a colloidal solution addition section 120, the centrifugation section 130, a supernatant fraction-acquiring section 140, an imaging section 150, and a fluid recovery section 160.

The sieving section 110 is a unit for sieving the sample 1 including the biological particles as a detection target and acquiring a fraction (1b) which passes through the sieve (A) and does not pass through the sieve (B). The sieve (A) has larger meshes than the sieve (B). The sieve (A) is for removing particles larger than the biological particles as a detection target. It is possible to appropriately select the meshes of the sieve (A) based on the size of the biological particles as a detection target. However, the meshes of the sieve (A) are set to be the maximum value or less of the size able to pass through the flow cell of the imaging section 150. Specifically, the sieve (A) has meshes smaller than whichever is larger of either of the inner diameter in the width direction and in the depth direction of the flow cell. Alternatively, the meshes of the sieve (A) may be meshes smaller than the maximum size through which biological particles are able to pass in the flow path design of the flow cell.

The sieve (B) has smaller meshes than the sieve (A). The sieve (B) is for removing particles smaller than the biological particles as a detection target. It is possible to appropriately select the meshes of the sieve (B) based on the size of the biological particles as a detection target. However, the sieve (B) preferably has meshes which are the minimum value or less of the particle diameter on which the camera of the imaging section 150 is able to focus. The minimum value of the particle diameter on which the camera of the imaging section 150 is able to focus is defined by the inner diameter in the depth direction of the flow cell provided in the imaging section 150 and the depth of focus of the camera. Accordingly, the meshes of the sieve (B) may be selected based on the size of the biological particles as a detection target, the inner diameter in the depth direction of the flow cell, and the depth of focus of the camera.

For example, it is possible to generally express the depth of focus of a camera by Berek's formula, as shown in Equation (1).

(Equation 1)

$$D.O.F = \frac{\omega \times 250{,}000}{NA \times M} + \frac{\lambda}{2(NA)^2} (\mu m) \quad (1)$$

D.O.F: Depth of Focus
ω: Resolving power of eyes (0.014: in a case where optical angle of the eye is set to 5 parts)
M: Total magnification
λ: Wavelength of light (λ=0.55 μm in the case of visible light)
NA: Numerical aperture defined by camera Here, for example, when M=1000 and NA=0.90, D.O.F.=0.73 μm. Also, for example, when M=4 and NA=0.90, D.O.F.=182.5 μm.

In addition, in a case of a ½-inch HD camera, the CCD size is 6.4 mm (W)×4.8 mm (H), the CCD pixel number is 1980 (W)×1080 (H), and the resolution has a width (W) of 3.2 μm and a height (H) of 4.4 μm. Accordingly, when M=4, the minimum value of the particle diameter on which the camera is able to focus is 0.8 μm in width (W) and 1.1 μm in height (H).

When the depth of focus and the camera specification are set in this manner, the total magnification (M) is determined, and the minimum value of the particle diameter on which the camera is able to focus is determined.

Since the limit resolution in the optical system is 0.2 μm, the meshes of the sieve (B) may be 0.2 μm or more. For example, the meshes of the sieve (B) may be 1 μm or more, 10 μm or more, or 20 μm or more in accordance with the details of the biological particles as a detection target.

In a case where the biological particles as a detection target are meiofauna, examples thereof include 250 to 1000 μm as meshes of the sieve (A) and 32 to 62 μm as meshes of the sieve (B).

Based on the size of the biological particles as a detection target, the size of the flow cell, and the depth of focus of the camera, the operator selects appropriate meshes for each of the sieve (A) and the sieve (B), which may be installed in the sieving section 110. Alternatively, the sieving section 110 may be provided with a plurality of types of sieves having different meshes, and the sieve (A) and the sieve (B) may be selected according to the size of the biological particles as a detection target and the flow cell, and the depth of focus of the camera. In such a case, depending on the selection by the operator, the sieve (A) and the sieve (B) may be installed in the sieving section 110. Alternatively, the biological particle image-acquiring apparatus 200 may automatically select the sieve (A) and the sieve (B) according to the size of the biological particles as a detection target and the flow cell, and the depth of focus of the camera, and install the sieve (A) and the sieve (B) in the sieving section 110. The biological particle image-acquiring apparatus 200 may be provided with an input unit or the like for inputting the size of the biological particles as a detection target, the size of the flow cell, the depth of focus of the camera, and the like.

It is possible for other configurations of the sieving section 110 to be the same as described in the pretreatment apparatus 100 for a sample including biological particles.

The colloidal solution addition section 120, the centrifugation section 130, and the supernatant fraction-acquiring section 140 are the same as described in the pretreatment apparatus 100 for a sample including biological particles.

The imaging section 150 is a unit for imaging the fluid flowing in the flow cell with a camera while allowing the fluid 4 including at least a part of the supernatant fraction (S0) acquired by the supernatant fraction-acquiring section 140 to flow in the flow cell. The imaging section 150 includes at least a flow cell and a camera.

For example, the imaging section 150 may have a configuration as shown in FIG. 6d. In the example of FIG. 6d, there is a configuration in which the flow cell 31 and the camera 32 are provided, the objective lens 33 is installed between the flow cell 31 and the camera 32, and the camera 32 images the frame 40 portion of the flow cell 31 via the objective lens 33. In addition, light is irradiated on the frame 40 portion by the light source 34.

The flow cell 31 may be appropriately selected according to the biological particles as the detection target. For example, in a case where the detection target is meiofauna, it is possible to set the inner diameter of the flow cell 31 in the depth direction with respect to the imaging plane to 150 to 500 μm. In addition, a pump or the like may be connected to the downstream side of the flow cell 31, and the fluid introduced into the flow cell 31 may be suctioned by the pump or the like to create a fluid flow in the flow cell 31.

The camera 32 may be for a still image or may be for a moving image. In a case where the camera 32 is for a still image, it is preferable that continuous imaging be possible, and it is more preferable to perform continuous imaging at predetermined time intervals. In addition, the imaging interval may be set by an operation panel or the like.

The objective lens 33 is used to acquire an enlarged image of the frame 40. The magnification of the objective lens 33 may be appropriately selected according to the biological particles as the detection target. For example, in a case where the detection target is meiofauna, it is possible to use an objective lens with a magnification of 10 to 100 times.

The light source 34 is used to irradiate the frame 40 with light to acquire a clearer image. The light source 34 may intermittently irradiate light according to the imaging interval by the camera 32 or may constantly irradiate light, but is preferably a flash light source which irradiates light at predetermined intervals. In addition, the irradiation interval may be set by an operation panel or the like.

Light irradiated from the light source 34 is not particularly limited, but is preferably visible light. In addition, in a case where the biological particles as the detection target are stained with a fluorescent dye, the biological particles may be irradiated with light having a wavelength exciting the fluorescent dye.

A description will be given of an example of the operation of the biological particle image-acquiring apparatus 200 provided with the above configuration.

First, the sample 1 including biological particles as a detection target is put into the sieving section 110. In the sieving section 110, the sample 1 is sieved, and a fraction (1b) which passes through the sieve (A) and does not pass through the sieve (B) is acquired. Many of the sediment particles included in the sample 1 are removed by sieving in the sieving section 110.

The colloidal solution 2 is added to the fraction (1b) acquired by the sieving section 110 by the colloidal solution addition section 120. Due to this, the mixture 3 of the fraction (1b) and the colloidal solution 2 is prepared.

The mixture 3 is introduced into the centrifugation section 130 and subjected to centrifugation. Due to this, the mixture 3 is separated into a supernatant fraction (S0) and a precipitate (P0). The supernatant fraction (S0) includes the biological particles as the detection target and the precipitate (P0) includes sediment particles. It is possible to acquire a supernatant fraction (S0) including almost no sediment particles by centrifugation in the centrifugation section 130. Thereafter, the supernatant fraction (S0) is acquired by the supernatant fraction-acquiring section 140 and appropriately prepared as the fluid 4 including at least a part of the supernatant fraction (S0).

The fluid 4 is introduced into the imaging section 150 and imaged. In the imaging section 150, the fluid 4 flows in the flow cell and an image of the fluid present in the imaging frame on the flow cell is imaged by the camera. In this manner, it is possible for the biological particle image-acquiring apparatus 200 to acquire images of biological particles as the detection target.

Since the biological particle image-acquiring apparatus of the present embodiment has the configuration described above, it is possible to acquire an image having sufficient image quality for subsequent analysis even with a sample including a lot of sediment particles. In addition, since it is possible to automatically perform the operations up to image acquisition, it is possible to eliminate the time and effort required in the related art for analysis by a microscope.

The biological particle image-acquiring apparatus 200 may be provided with other configurations than the above configuration. In the example shown in FIG. 9, the biological particle image-acquiring apparatus 200 is provided with the fluid recovery section 160.

The fluid recovery section 160 is a unit for recovering the fluid 4 for which the imaging in the imaging section 150 is finished. For example, it is possible for the fluid recovery section 160 to have a configuration provided with a container for recovering the fluid 4, a tube for guiding the fluid 4 to the container, a pump for making a flow of the fluid 4 in the tube, and the like. For example, it is possible to have a configuration in which a tube is connected to the downstream end of the flow cell 31 in the imaging section 150, and the tube is connected to a container in the fluid recovery section 160. In addition, a configuration may be adopted in which a pump is connected to the container, the air in the container is discharged, and the fluid 4 which has passed through the flow cell is recovered in the container via the tube.

It is possible to use the fluid 4 recovered by the fluid recovery section 160 for further analysis.

In addition, the biological particle image-acquiring apparatus 200 may be provided with a precipitation suspension section, a supernatant fraction preparation sections, and the like in the same manner as the pretreatment apparatus 100 for a sample including biological particles. The precipitation suspension section and the supernatant fraction preparation section are the same as described in the pretreatment apparatus 100.

It is possible for the biological particle image-acquiring apparatus 200 to further include an image display section which displays the image acquired by the imaging section 150, an image analysis section which analyzes the acquired image, a control section which controls the operation of the entire device, and the like.

EXAMPLES

A description will be given below of the present invention with reference to Examples, but the present invention is not limited to the following Examples.

Test Example 1

[Samples for Analysis]

Sediment samples obtained at three points (water depth 560 m, 3300 m, and 7100 m) off Kushiro, Hokkaido, were used.

[Sieving of Samples]

The sediment samples were sieved using six sieves with meshes of 1 mm, 500 μm, 250 μm, 125 μm, 63 μm, and 38 μm. The number of meiofauna captured by each of the sieves was confirmed by a microscope.

[Results]

Table 1 shows the number of meiofauna captured by each sieve. Approximately 80% of the individuals were in the sieving section of 63 to 250 μm.

TABLE 1

| Sieve meshes | Water depth: 560 m | | Water depth: 3300 m | | Water depth: 7100 m | |
|---|---|---|---|---|---|---|
| | Population density (ind./ 10 cm$^2$) | Ratio (%) | Population density (ind./ 10 cm$^2$) | Ratio (%) | Population density (ind./ 10 cm$^2$) | Ratio (%) |
| >1 mm | 1.12 | 0.36 | 0.74 | 0.19 | 0.74 | 0.34 |
| >500 μm | 5.95 | 1.90 | 2.97 | 0.78 | 2.97 | 1.37 |
| >250 μm | 44.97 | 14.40 | 16.35 | 4.27 | 11.89 | 5.50 |
| >125 μm | 123.40 | 39.52 | 169.49 | 44.27 | 99.61 | 46.05 |
| >63 μm | 110.02 | 35.24 | 145.70 | 38.06 | 65.42 | 30.24 |
| >38 μm | 26.76 | 8.57 | 47.58 | 12.43 | 35.68 | 16.49 |

Test Example 2

[Samples for Analysis]

Sediment samples obtained at 4 points (water depth 72 m, 303 m, 1064 m, 1677 m) off Otsuchi Bay, Iwate prefecture, were used.

[Sample Pretreatment for Acquiring Analysis Image]

The sediment samples were fixed with 5% neutralized formalin and the organisms in the sediment samples were stained with Rose Bengal (final concentration 0.05 g/L).

Approximately 26.4 mL of the sediment samples after the dyeing operation was sieved while shaking. For sieving, a sieve having meshes of 250 μm and a sieve having meshes of 63 μm were used and samples which had passed through a sieve having meshes of 250 μm and did not pass through a sieve having meshes of 63 μm were recovered.

The recovered sample was placed in a 50-mL centrifuge tube and approximately 30 mL of colloidal silica (LUDOX HS-40, SIGMA-ALDRICH) was added thereto to suspend the sample in the colloidal silica. Thereafter, the sample was centrifuged at 800 G for 10 minutes using a centrifugal separator (L.C 200, TOMY). The supernatant was collected from the centrifuge tube after centrifugation and collected on a sieve having meshes of 32 μm.

After collecting the supernatant, approximately 30 mL of colloidal silica was added to the precipitate in the centrifuge tube, and the precipitate was suspended in the colloidal silica. Thereafter, the sample was centrifuged at 800 G for 10 minutes using a centrifugal separator. The supernatant was collected from the centrifuge tube after centrifugation and collected on a sieve having meshes of 32 μm. The operation was performed one more time.

A sample collected on a sieve having meshes of 32 μm from the above-described supernatant after three centrifugations was suspended in approximately 10 ml of colloidal silica and recovered in a new 50-mL centrifuge tube.

[Acquisition of Analysis Images]

The acquisition of analysis images was performed using FlowCAM (Fluid Imaging Technologies), a counting device of flowing particle with a camera. An objective lens having a magnification of four times was used, and a flow cell having an inner diameter of 300 μm in the depth direction with respect to the imaging plane of the camera was used.

In addition, in order to recover the sample passed through FlowCAM, a new 50-mL centrifuge tube was prepared. The upper portion of the centrifuge tube was hermetically sealed with parafilm, two tubes were inserted, and the other end of one tube was connected to the downstream side of the flow cell. The other end of the other tube was connected to a peristatic pump (Fisher Scientific). With this configuration, when the peristatic pump is operated, a sample flows from the flow cell to the tube, and the sample is recovered in the centrifuge tube. In this manner, the sample which had passed through the FlowCAM was collected in a centrifuge tube.

The flow cell and the tube connected to the flow cell were filled in advance with a colloidal silica solution before the introduction of the sample.

In the configuration as described above, the sample recovered in the centrifuge tube was gently stirred, introduced into a FlowCAM flow cell using a Pasteur pipette, and imaged. Imaging was performed in Auto Image Mode, and the Auto image Rate (the number of images imaged per second) was set to 20. In addition, the Flash Duration was set to 10 μs.

[Image Analysis]

The imaged image was sorted by the sort function Red/Blue Ratio of the software VisualSpreadSheet attached to FlowCAM, each image was confirmed visually, and the organisms were selected and counted for each higher classification group. Here, although the selection was performed visually, biological images may be automatically selected and classified by a program or the like from the form of the organisms obtained from each image and the morphological features such as spines. The selection of biological images may be performed by image analysis software, artificial intelligence (A.I.), or the like.

[Results]

The centrifuge tube used for introducing the sample into FlowCAM and the inside of the tube after finishing counting were examined, and there were a few organisms remaining.

FIGS. 5a to 5e show examples of images imaged by FlowCAM. The images captured with FlowCAM were sufficient quality to select the organisms visually.

Figure 11:
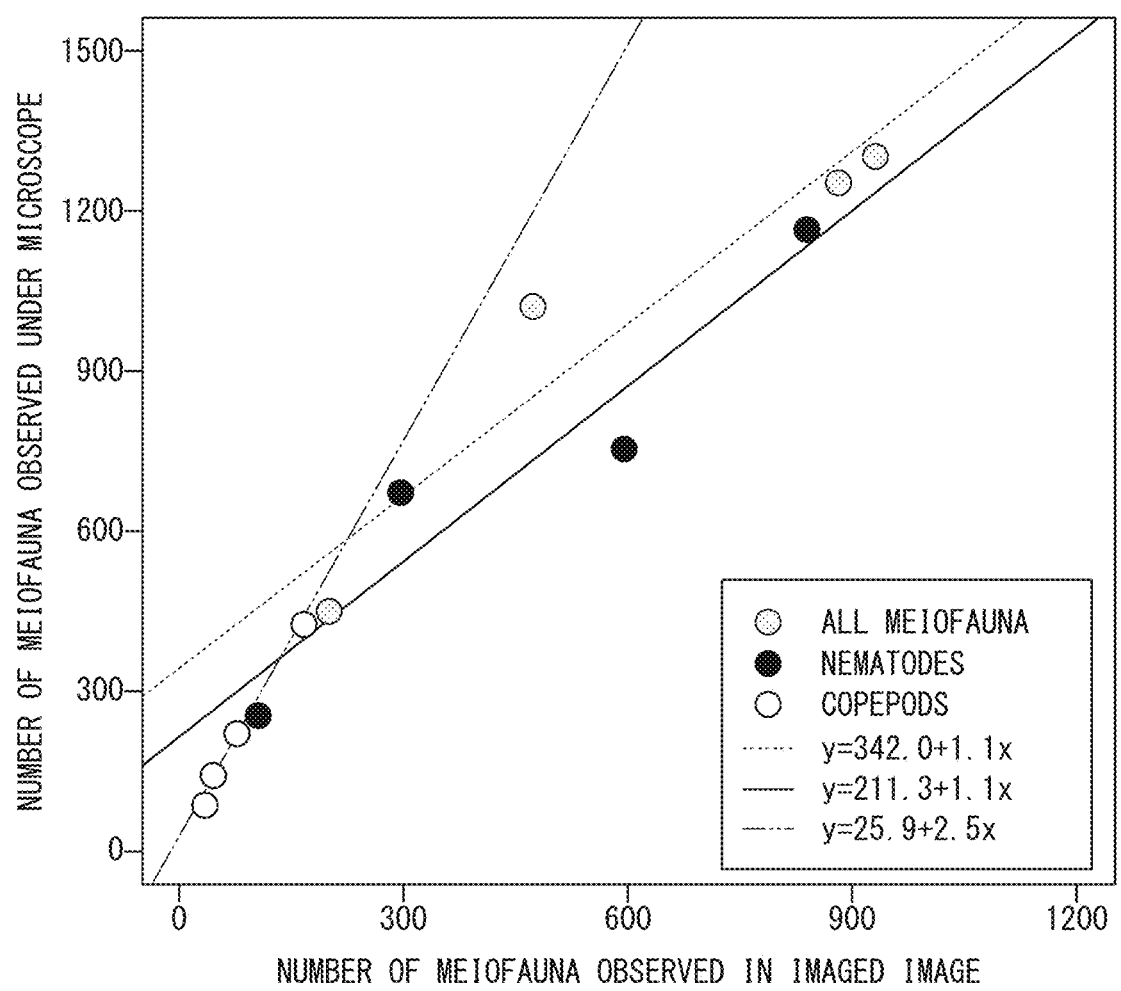
FIG. 11 shows correlations between a population of meiofauna counted based on an image acquired by the method according to one embodiment of the present invention and a population counted under a microscope.

The imaging efficiency was calculated by comparing the number of organisms observed in FlowCAM with the number collected in the centrifuge tube after passing through FlowCAM. As a result, the imaging efficiency was 57.9±14.8% for the meiofauna as a whole, 58.9±19.6% for the nematodes, and 34.6±3.7% for the copepods. In addition, the number counted with FlowCAM and the number counted by the microscope with the sample collected in the centrifuge tube showed a significant correlation (total meiofauna: r=0.95, p<0.05; nematodes: r=0.95, p<0.05; copepods: r=1.00, p<0.01; FIG. 11).

From the above, it is clear that this method is able to obtain analysis results with a high correlation with the analysis results of the number of organisms obtained by the microscopic methods of the related art.

INDUSTRIAL APPLICABILITY

According to the present invention, a technique is provided which is capable of quickly analyzing biological particles even in a case where sediment particles are present.

REFERENCE SIGNS LIST

1 SAMPLE
1a FRACTION WHICH DOES NOT PASS THROUGH A SIEVE HAVING MESHES OF 250 TO 1000 μm
1b FRACTION WHICH PASSES THROUGH A SIEVE HAVING MESHES OF 250 TO 1000 μM AND DOES NOT PASS THROUGH A SIEVE HAVING MESHES OF 32 TO 63 μm
1c FRACTION WHICH PASSES THROUGH A SIEVE HAVING MESHES OF 32 TO 63 μm
2 COLLOIDAL SOLUTION
3 MIXTURE INCLUDING FRACTIONS (1b) AND COLLOIDAL SOLUTION 2

4 FLUID
5a to 5c BIOLOGICAL PARTICLES
6 SUSPENSION
10 CONTAINER
13 SHAKER
20 CENTRIFUGE
21 CENTRIFUGE TUBE
30 IMAGING APPARATUS
31 FLOW CELL
32 CAMERA
33 OBJECTIVE LENS
34 LIGHT SOURCE
40 FRAMES
41 IMAGE
100 APPARATUS FOR PRETREATING SAMPLE INCLUDING BIOLOGICAL PARTICLES
110 SIEVING SECTION
120 COLLOIDAL SOLUTION ADDITION SECTION
130 CENTRIFUGATION SECTION
140 SUPERNATANT FRACTION-ACQUIRING SECTION
150 IMAGING SECTION
160 FLUID RECOVERY SECTION
200 BIOLOGICAL PARTICLE IMAGE-ACQUIRING APPARATUS
A SIEVE HAVING MESHES OF 250 TO 1000 μm
B SIEVE HAVING MESHES OF 32 TO 63 μm
S0 to Sn SUPERNATANT FRACTION
P0 to Pn PRECIPITATION
90 INTEGRATION SYSTEM
910 REFERENCE DATABASE
920 BIOLOGICAL IMAGE ACQUIRING DEVICE
930 BIOLOGICAL INFORMATION DETERMINATION DEVICE
940 IMAGE DATABASE
950 NUCLEOTIDE SEQUENCE INFORMATION ACQUIRING DEVICE
960 NUCLEOTIDE SEQUENCE INFORMATION DETERMINATION DEVICE
970 NUCLEOTIDE SEQUENCE INFORMATION DATABASE
980 INTEGRATION DEVICE
990 AN INTEGRATED DATABASE
800 ANALYSIS DEVICE

The invention claimed is:

1. An integration system comprising:
a central processing unit, the central processing unit accessing a program from memory, the program being executable by the central processing unit including
a biological image acquiring device which acquires, from a sample including biological particles which are a detection target, a biological image which is an image of the biological particles;
a nucleotide sequence information acquiring device which acquires nucleotide sequence information of the biological particles;
an integration device which associates and registers the biological image and the nucleotide sequence information acquired from the same type of biological particles in an integrated database;
a biological information determination device which acquires information relating to a population for each type of the biological particles in the sample based on an image acquired by the biological image acquiring device; and
a nucleotide sequence information determination device which acquires information relating to the population for each type of the biological particles in the sample based on nucleotide sequence information acquired by the nucleotide sequence information acquiring device,
wherein the integration device associates and registers the information relating to the population obtained based on the image and the information relating to the population obtained based on the nucleotide sequence information in the integrated database in addition to the biological image and the nucleotide sequence information;
the biological information determination device which acquires first individual information which is information relating to a population for each type of the biological particles in the sample based on an image acquired by the biological image acquiring device; and
the nucleotide sequence information determination device which acquires second individual information which is information relating to a population for each type of the biological particles in the sample based on nucleotide sequence information acquired by the nucleotide sequence information acquiring device,
wherein the integration device associates and registers the image corresponding to the first individual information and the nucleotide sequence information corresponding to the second individual information in the integrated database when the first individual information and the second individual information are determined to be similar information based on predetermined criteria, and
wherein the fact that the first individual information and the second individual information are similar signifies that the images and the nucleotide sequence information of approximately the same population were acquired in the sample.

2. An integration system comprising:
a central processing unit, the central processing unit accessing a program from memory, the program being executable by the central processing unit including:
a biological image acquiring device which acquires, from a sample including biological particles which are a detection target, a biological image which is an image of the biological particles;
a nucleotide sequence information acquiring device which acquires nucleotide sequence information of the biological particles;
an integration device which associates and registers the biological image and the nucleotide sequence information acquired from the same type of biological particles in an integrated database;
a biological information determination device which acquires first individual information which is information relating to a population for each type of the biological particles in the sample based on an image acquired by the biological image acquiring device; and
a nucleotide sequence information determination device which acquires second individual information which is information relating to a population for each type of the biological particles in the sample based on nucleotide sequence information acquired by the nucleotide sequence information acquiring device,
wherein the integration device associates and registers the image corresponding to the first individual information and the nucleotide sequence information corresponding to the second individual information in the integrated database when the first individual information and the second individual information are determined to be similar information based on predetermined criteria, and wherein the fact that the first individual information and the second individual information are similar signifies that the images and the nucleotide sequence information of approximately the same population were acquired in the sample.

3. An integration system comprising:

a central processing unit, the central processing unit accessing a program from memory, the program being executable by the central processing unit including a biological image acquiring device which acquires, from a sample including biological particles which are a detection target, a biological image which is an image of the biological particles;

a nucleotide sequence information acquiring device which acquires nucleotide sequence information of the biological particles;

an integration device which associates and registers the biological image and the nucleotide sequence information acquired from the same type of biological particles in an integrated database;

a biological information determination device which acquires a value indicating an application ratio which is a ratio of a population of each type with respect to a population of all types of biological particles detected from the sample based on an image acquired by the biological image acquiring device; and a nucleotide sequence information determination device which acquires a value indicating an application ratio which is a ratio of the population of each type with respect to the population of all types of biological particles detected from the sample based on nucleotide sequence information acquired by the nucleotide sequence information acquiring device, wherein the integration device associates and registers a value indicating an appearance ratio obtained based on the image and a value indicating an appearance ratio obtained based on the nucleotide sequence information in the integrated database, in addition to the biological image and the nucleotide sequence information, the biological information determination device which acquires first individual information which is information relating to a population for each type of the biological particles in the sample based on an image acquired by the biological image acquiring device;

the nucleotide sequence information determination device which acquires second individual information which is information relating to a population for each type of the biological particles in the sample based on nucleotide sequence information acquired by the nucleotide sequence information acquiring device, wherein the integration device associates and registers the image corresponding to the first individual information and the nucleotide sequence information corresponding to the second individual information in the integrated database when the first individual information and the second individual information are determined to be similar information based on predetermined criteria, and wherein the fact that the first individual information and the second individual information are similar signifies that the images and the nucleotide sequence information of approximately the same population were acquired in the sample.

4. The integration system according to claim 1, wherein, in a state in which a fluid including the sample flows in a flow cell, the biological image acquiring device acquires the biological image by imaging the fluid.

5. The integration system according to claim 1, further comprising:

an analysis device for identifying the nucleotide sequence information of the biological particles of a newly acquired biological image or identifying a biological image of nucleotide sequence information of a newly acquired organism based on association between the biological image and the nucleotide sequence information registered in the integrated database.

6. The integration system according to claim 5, wherein the analysis device carries out identification further based on obtained attribute information relating to the biological particles.

7. The integration system according to claim 1, wherein the integration device estimates a classification group of the biological particles based on the biological image or the nucleotide sequence information.

8. The integration system according to claim 5, wherein the analysis device determines a growth state of the biological particles based on the biological image and determines a type of the biological particles based on the nucleotide sequence information.

9. An integration method comprising:

accessing, by a central processing unit, a program from memory, the program being executable by the central processing unit including:

a biological image acquiring step of acquiring, from a sample including biological particles, which are a detection target, a biological image which is an image of the biological particles;

a nucleotide sequence information acquiring step of acquiring nucleotide sequence information of the biological particles;

an integration step of associating and registering the biological image and the nucleotide sequence information acquired from biological particles of the same type in an integrated database;

a biological information determination step of acquiring a value indicating an application ratio which is a ratio of a population of each type with respect to a population of all types of biological particles detected from the sample based on an image acquired in the biological image acquiring step; and a nucleotide sequence information determination step of acquiring a value indicating an application ratio which is a ratio of the population of each type with respect to the population of all types of biological particles detected from the sample based on nucleotide sequence information acquired in the nucleotide sequence information acquiring step, wherein the integration step associates and registers a value indicating an appearance ratio obtained based on the image and a value indicating an appearance ratio obtained based on the nucleotide sequence information in the integrated database, in addition to the biological image and the nucleotide sequence information, a biological information determination step of acquiring first individual information which is information relating to a population for each type of the biological particles in the sample based on an image acquired by the biological image acquiring device;

a nucleotide sequence information determination step of acquiring second individual information which is information relating to a population for each type of the biological particles in the sample based on nucleotide sequence information acquired by the nucleotide sequence information acquiring device, wherein the integration step associates and registers the image corresponding to the first individual information and the nucleotide sequence information corresponding to the second individual information in the integrated database when the first individual information and the second individual information are determined to be similar information based on predetermined criteria, and wherein the fact that the first individual information and the second individual information are similar signifies that the images and the nucleotide sequence information of approximately the same population were acquired in the sample.

10. The integration system according to claim 3, wherein, in a state in which a fluid including the sample flows in a flow cell, the biological image acquiring device acquires the biological image by imaging the fluid.

11. The integration system according to claim 3, further comprising:

an analysis device for identifying the nucleotide sequence information of the biological particles of a newly acquired biological image or identifying a biological image of nucleotide sequence information of a newly acquired organism based on association between the biological image and the nucleotide sequence information registered in the integrated database.

12. The integration system according to claim 3, wherein the integration device estimates a classification group of the biological particles based on the biological image or the nucleotide sequence information.

* * * * *